(12) United States Patent
Bonne et al.

(10) Patent No.: US 7,502,109 B2
(45) Date of Patent: Mar. 10, 2009

(54) OPTICAL MICRO-SPECTROMETER

(75) Inventors: Ulrich Bonne, Hopkins, MN (US);
James Detry, Plymouth, MN (US);
Teresa Marta, White Bear Lake, MN
(US); Klein Johnson, Orono, MN (US)

(73) Assignee: Honeywell International Inc.,
Morristown, NJ (US)

( * ) Notice: Subject to any disclaimer, the term of this patent is extended or adjusted under 35 U.S.C. 154(b) by 163 days.

(21) Appl. No.: 11/383,723

(22) Filed: May 16, 2006

(65) Prior Publication Data
US 2006/0262303 A1 Nov. 23, 2006

Related U.S. Application Data

(60) Provisional application No. 60/681,776, filed on May 17, 2005, provisional application No. 60/743,486, filed on Mar. 15, 2006.

(51) Int. Cl.
*G01J 3/28* (2006.01)
(52) U.S. Cl. ........................................................ 356/328
(58) Field of Classification Search .................. 356/328
See application file for complete search history.

(56) References Cited

U.S. PATENT DOCUMENTS

| 906,468 | A | 12/1908 | Steynis |
| 1,157,859 | A | 10/1915 | Freet |
| 1,454,219 | A | 5/1923 | Goedicke |
| 1,505,669 | A | 8/1924 | Quain |
| 3,146,616 | A | 9/1964 | Loyd |
| 3,557,532 | A | 1/1971 | Broerman |
| 3,730,874 | A | 5/1973 | Trub |
| 3,783,356 | A | 1/1974 | Lide, III et al. |
| 3,833,492 | A | 9/1974 | Bollyky |
| 3,921,002 | A | 11/1975 | Williams et al. |

(Continued)

FOREIGN PATENT DOCUMENTS

DE 2934566 3/1981

(Continued)

OTHER PUBLICATIONS

Amano, "Infrared spectroscopic detection of ions and free radicals in discharge plasmas," pp. 72-82, SPIE Proceedings, vol. 1858, 1993.

(Continued)

*Primary Examiner*—Kara E Geisel
(74) *Attorney, Agent, or Firm*—Kris T. Fredrick

(57) ABSTRACT

An optical spectrometer having a multi-wafer structure. The structure may be fabricated with MEMS technology. The spectrometer may be integrated with a fluid analyzer. A reflective grating such as a diffraction or holographic grating situated on the circumference of a Rowland circle along with a point of light emission and a detector may be a configuration of the spectrometer. Some configurations may use an external light source where the light may be optically conveyed to the point of emission on the circle. There may be a Raman configuration where an interaction of light with a sample or an interactive film of a channel in a fluid analyzer is the point of light emission for the spectrometer. In some configurations of the spectrometer, the grating and/or the film may be reflective or transmissive.

13 Claims, 18 Drawing Sheets

U.S. PATENT DOCUMENTS

| | | | |
|---|---|---|---|
| 3,967,131 A | 6/1976 | Slipiec et al. | |
| 4,025,441 A | 5/1977 | Tabata et al. | |
| 4,043,196 A | 8/1977 | Trageser | |
| 4,048,668 A | 9/1977 | Von Bargen et al. | |
| 4,049,552 A | 9/1977 | Arff | |
| 4,051,045 A | 9/1977 | Yamamoto et al. | |
| 4,079,260 A | 3/1978 | Dmitriev et al. | |
| 4,101,783 A | 7/1978 | Hutter | |
| 4,123,664 A | 10/1978 | Yamamura et al. | |
| 4,128,768 A | 12/1978 | Yamamoto et al. | |
| 4,159,971 A | 7/1979 | Gneupel | |
| 4,216,096 A | 8/1980 | Pare et al. | |
| 4,228,815 A | 10/1980 | Juffa et al. | |
| 4,234,800 A | 11/1980 | Kenly, V et al. | |
| 4,324,566 A | 4/1982 | Jacob et al. | |
| 4,383,976 A | 5/1983 | Notaro | |
| 4,411,756 A | 10/1983 | Bennett et al. | |
| 4,417,966 A | 11/1983 | Krauss et al. | |
| 4,461,744 A | 7/1984 | Erni et al. | |
| 4,478,076 A | 10/1984 | Bohrer | |
| 4,483,200 A | 11/1984 | Togawa et al. | |
| 4,504,446 A | 3/1985 | Kunicki et al. | |
| 4,507,974 A | 4/1985 | Yelderman | |
| 4,576,050 A | 3/1986 | Lambert | |
| 4,614,573 A | 9/1986 | Masuda | |
| 4,640,782 A | 2/1987 | Burleson | |
| 4,650,573 A | 3/1987 | Nathanson | |
| 4,656,010 A | 4/1987 | Leitzke et al. | |
| 4,690,803 A | 9/1987 | Hirth | |
| 4,696,800 A | 9/1987 | Sasaki et al. | |
| 4,725,412 A | 2/1988 | Ito | |
| 4,735,082 A | 4/1988 | Kolloff | |
| 4,759,210 A | 7/1988 | Wohltjen | |
| 4,764,349 A | 8/1988 | Arff et al. | |
| 4,877,588 A | 10/1989 | Ditzler et al. | |
| 4,886,645 A | 12/1989 | Fischer et al. | |
| 4,909,078 A | 3/1990 | Sittler et al. | |
| 4,944,035 A | 7/1990 | Aagardl et al. | |
| 4,960,569 A | 10/1990 | Fovell et al. | |
| 4,981,656 A | 1/1991 | Leitke | |
| 5,004,587 A | 4/1991 | Tacchi | |
| 5,008,087 A | 4/1991 | Batchelor | |
| 5,031,126 A | 7/1991 | McCulloch et al. | |
| 5,034,198 A | 7/1991 | Kaiga et al. | |
| 5,044,766 A | 9/1991 | Stuart | |
| 5,056,047 A | 10/1991 | Sondergeld | |
| 5,093,087 A | 3/1992 | Freeman | |
| 5,124,132 A | 6/1992 | Francis, Jr. et al. | |
| 5,135,549 A | 8/1992 | Phillips et al. | |
| 5,145,653 A | 9/1992 | Fischer et al. | |
| 5,146,414 A | 9/1992 | McKown et al. | |
| 5,196,039 A | 3/1993 | Phillips et al. | |
| 5,225,681 A * | 7/1993 | Falk et al. | 250/372 |
| 5,243,858 A | 9/1993 | Erskine et al. | |
| 5,263,380 A | 11/1993 | Sultan et al. | |
| 5,268,151 A | 12/1993 | Reed et al. | |
| 5,268,302 A | 12/1993 | Rounbehler et al. | |
| 5,379,630 A | 1/1995 | Lacey | |
| 5,411,713 A | 5/1995 | Iwanaga | |
| 5,442,175 A | 8/1995 | Dawson | |
| 5,463,899 A | 11/1995 | Zemel et al. | |
| 5,469,013 A | 11/1995 | Kang | |
| 5,506,149 A * | 4/1996 | Crawford et al. | 436/171 |
| 5,533,412 A | 7/1996 | Jerman et al. | |
| 5,587,520 A | 12/1996 | Rhodes | |
| 5,591,896 A | 1/1997 | Lin | |
| 5,665,604 A | 9/1997 | Monagle et al. | |
| 5,922,974 A | 7/1999 | Davison et al. | |
| 5,937,113 A * | 8/1999 | He et al. | 385/11 |
| 6,016,027 A | 1/2000 | DeTemple et al. | |
| 6,081,331 A * | 6/2000 | Teichmann | 356/328 |
| 6,097,863 A * | 8/2000 | Chowdhury | 385/37 |
| 6,131,440 A | 10/2000 | Bertrand | |
| 6,139,384 A | 10/2000 | DeTemple et al. | |
| 6,169,965 B1 | 1/2001 | Kubisiak et al. | |
| 6,178,811 B1 | 1/2001 | Bonne et al. | |
| 6,181,418 B1 * | 1/2001 | Palumbo et al. | 356/328 |
| 6,194,833 B1 | 2/2001 | DeTemple et al. | |
| 6,308,553 B1 | 10/2001 | Bonne et al. | |
| 6,393,894 B1 | 5/2002 | Bonne et al. | |
| 6,413,781 B1 | 7/2002 | Geis et al. | |
| 6,455,842 B1 * | 9/2002 | Pouteau et al. | 250/227.18 |
| 6,457,347 B1 | 10/2002 | Koo et al. | |
| 6,469,785 B1 * | 10/2002 | Duveneck et al. | 356/244 |
| 6,494,617 B1 | 12/2002 | Stokes et al. | |
| 6,524,538 B2 | 2/2003 | Barankova et al. | |
| 6,547,347 B2 | 4/2003 | Saito et al. | |
| 6,606,156 B1 * | 8/2003 | Ehbets et al. | 356/328 |
| 6,657,370 B1 | 12/2003 | Geusic | |
| 6,657,723 B2 * | 12/2003 | Cohen et al. | 356/328 |
| 6,666,907 B1 | 12/2003 | Manginell et al. | |
| 6,753,958 B2 * | 6/2004 | Berolo et al. | 356/328 |
| 6,837,118 B2 | 1/2005 | Bonne et al. | |
| 6,892,002 B2 * | 5/2005 | Christoffersen et al. | 385/39 |
| 6,904,205 B2 * | 6/2005 | Berolo et al. | 385/37 |
| 7,000,452 B2 | 2/2006 | Bonne et al. | |
| 7,034,935 B1 * | 4/2006 | Kruzelecky | 356/328 |
| 7,081,955 B2 * | 7/2006 | Teichmann et al. | 356/328 |
| 7,092,090 B2 * | 8/2006 | Shimizu et al. | 356/328 |
| 7,199,876 B2 * | 4/2007 | Mitchell | 356/328 |
| 7,327,908 B1 * | 2/2008 | Iazikov et al. | 385/12 |
| 7,330,614 B1 * | 2/2008 | Mossberg et al. | 385/14 |
| 2002/0068017 A1 | 6/2002 | Naatz et al. | |
| 2002/0139925 A1 | 10/2002 | Mitrovic | |
| 2004/0060346 A1 | 4/2004 | Bonne et al. | |
| 2004/0223882 A1 * | 11/2004 | Bonne et al. | 422/82.05 |
| 2004/0259265 A1 * | 12/2004 | Bonne | 436/151 |
| 2005/0042139 A1 * | 2/2005 | Bonne | 422/68.1 |
| 2005/0052648 A1 * | 3/2005 | Frick et al. | 356/328 |
| 2005/0063865 A1 | 3/2005 | Bonne et al. | |
| 2005/0093417 A1 * | 5/2005 | Gianchandani et al. | 356/316 |
| 2005/0142035 A1 * | 6/2005 | Bonne et al. | 422/82.05 |
| 2005/0142662 A1 * | 6/2005 | Bonne | 436/149 |
| 2005/0151966 A1 * | 7/2005 | Packirisamy et al. | 356/328 |
| 2006/0038490 A1 * | 2/2006 | Eden et al. | 313/582 |
| 2006/0197960 A1 * | 9/2006 | Bazylenko | 356/491 |

FOREIGN PATENT DOCUMENTS

| | | |
|---|---|---|
| DE | 3234146 | 3/1984 |
| DE | 4222458 | 1/1994 |
| DE | 4243573 | 6/1994 |
| DE | 29607315 | 8/1996 |
| DE | 19619133 | 11/1997 |
| DE | 10133384 | 1/2003 |
| EP | 0192919 | 9/1986 |
| EP | 0232719 | 8/1987 |
| EP | 0348245 | 12/1989 |
| EP | 0364982 | 4/1990 |
| EP | 0419873 | 4/1991 |
| EP | 0468793 | 1/1992 |
| EP | 0702212 | 3/1996 |
| EP | 0773432 | 5/1997 |
| GB | 2287792 | 9/1995 |
| JP | 56153256 | 11/1981 |
| JP | 57131029 | 8/1982 |
| JP | 57206830 | 12/1982 |
| JP | 2003139611 | 5/2003 |
| WO | 9206369 | 4/1992 |
| WO | 9420825 | 9/1994 |
| WO | 9822793 | 5/1998 |

| | | |
|---|---|---|
| WO | 0061261 | 10/2000 |

OTHER PUBLICATIONS

Atalla et al., "Radiation Effects with the AC Heated Strip Technique for the Measurement of Thermal Properties of Liquids", High Temperatures—High Pressures, vol. 17, pp. 447-452, 1985.

Atalla et al., "Measurement of Thermal Properties of Liquids with an AC Heated-Wire Technique", International Journal of Thermophysics, vol. 2, No. 2, 10 pages, 1981.

Bonne et al., "Industrial Wireless Phased Sensor Phase 1. Feasibility Demonstration," Progress Report for 4th Quarter of 2002, pp. 1-17, Jan. 31, 2002.

Bonne et al., "Phased: a Faster, Smarter and More Affordable Gas Analysis Device," 16th International Forum on Process Analytical Chemistry, San Diego, CA., pp. 1-17, Jan. 22-25, 2002.

Bonne et al., "Phased, a Faster, Smarter and More Affordable Gas Analysis Device—Update," International Forum on Process Analytical Chemistry (IFPAC) Scottsdale, AZ, Jan. 21-24, 2003.

Bonne et al., "New Gas Composition and Trace Contaminant Sensors," GTI Natural Gas Technologies Conference, Orland, FL, Sep. 30-Oct. 2, 2002, pp. 1-12.

Bonne, et al., "Actuation-based microsensors," Smart Materials and Structures, 10, pp. 1185-1195, 2001.

Cabuz, C. et al., "Mesoscopic Sampler Based on 3-D Array of Electrostatically Activated Diaphragms," Proc. 10th Conf. S.S. S&A. Transducers '99 Jun. 7-12, 1999, Sendai, Japan.

Cabuz, C., et al., "The Dual Diaphragm Pump," IEEE, pp. 519-522, 2001.

Dipl.-Ing. Dr. techn. Wolfgang Wehrmann et al., "Korrelationstechnik", Expert Verlag, Grafenau, XP002094984, 173 pages, 1980.

Fuggerth, Endre, "Zone Gas Chromatography," Analytical Chemistry, 61, No. 14, pp. 1478-1485, 1989.

Herring, "Microdischarge-Based Detection Systems," DARPA Workshop on Micro Gas Analyzers, Monterey, CA., 8 pages, Dec. 2002.

http://www.oceanoptics.com/products/usb2000.asp, "USB2000 Miniature Fiber Optic Spectrometer," 4 pages, prior to May 16, 2006.

http://www.photomet.com/life_products.html, Photometrics Webpages, 2 pages, prior to May 16, 2006.

Honeywell Electronic Materials Interconnect Solutions, Thin Films—Dielectrics, Comparison of Solution and Film Properties, Advanced Products for IC Fabrication, 1 page.

http://www.advanced-polymers.com/star_center/technical_papers/reduction_in_effective_dielectric_constant.pdf, 1 page.

http://www.chrompack.com/cgi/applicsview?ap=A00607&Go=G0, NexTrieve document view, 2 pages, printed Dec. 26, 2002.

http://wwww.emd.horiba.com/engmease/mexa720nox, HORIBA Engine Measurement Division: MEXA-720Nox—Non-Sampling type Nox A . . . , 3 pages printed Oct. 1, 2004.

http://www.zoex.com/html/technote_kt030505-1.html, Zoex Corporation, "A New Window on the Che," 5 pages, printed Mar. 15, 2004.

International Search Report, PCT/US00/19924, mailed Mar. 5, 2001, 7 pages.

Kenndler, "Gas Chromatography," Institute for Analytical Chemistry, University of Vienna, pp. 1-34, Sep. 9, 1999.

Kindlund et al., "Quartz Crystal Gas Monitor With Gas Concentrating Stage," Sensors and Actuators, 6, pp. 1-17, 1984.

Lee et al., "The Study of Atmospheric Pressure Plasma byLarge Area Capillary Electrode and It's Application," E-MRS Spring Meeting 2002, Jun. 18-21, 2002, pp. 440-746. (Abstract attached).

Park et al., "Microdischarge Arrays: A New Family of Photonic Devices (Revised)," IEEE Journal on Selected Topics in Quantum Electronics, vol. 8, No. 2, pp. 387-394, Mar./Apr. 2002.

Park et al., "Photodetection in the visible, ultraviolet, and near-infrared with silicon microdischarge devices," Applied Physics Letters, vol. 81, No. 24, pp. 4529-4531, Dec. 9, 2002.

Park et al., "Arrays of silicon micro discharge devices with multicomponent dielectrics," Optics Letters, vol. 26, No. 22, pp. 1773-1775, Nov. 15, 2001.

Phillips et al., "Thermal Modulation: A Chemical Instrumentation Component of Potential Value in Improving Portability," Field Analytical Chemistry and Technology, 1(1): 23-29, 1996.

Que et al., "A Water Spectroscopy Microsystem with Integrated Discharge Source, Dispersion Optics, and Sample Delivery," IEEE, The 12th International Conference on Solid State Sensors, Actuators and Microsystems,Boston, 4 pages, Jun. 8-12, 2003.

Quimby et al., "Evaluation of a Microwave Cavity, Discharge Tube, and Gas Flow System of Combined Gas Chromatography—Atomic Emission Detection," Analytical Chemistry, vol. 62, No. 10, pp. 1027-1034, May 15, 1990.

Stevenson, "Wintergreen '97," The World of Separation Science, The 19th International Symposium on Capillary Chromatography and Electrophoresis, 11 pages printed Jul. 22, 2003.

Thompson et al., "Ultraviolet Absorption Coefficients of $CO_2$, CO, $O_2$, $H_2O$, $N_2O$, $NH_3$, NO, $SO_2$, and $CH_4$, between 1850 and 4000 A," Journal of Geophysical Research, vol. § 68, No. 24, pp. 6431-6436, Dec. 1963.

Toker et al., "Design and Development of a Fiber Optic TDI CCD-Based Slot-Scan Digital Mammography System," X-Ray Detector Physics and Applications II, Proceedings SPIE-The International Society for Optical Engineering, vol. 2009,pp. 246-252, Jul. 13-14, 1993.

Whitman et al., "Double-Injection Flow Injection Analysis Using Multivariate Calibration for Multicomponent Analysis," Analytical Chemistry 63 pp. 775-781, 1991.

* cited by examiner

| Original Sample | Emission Bands | Wavelengths in nm |
|---|---|---|
| NO, NO2 | NO | 226.94, 237.02 and 247.87 |
| SO2 | SN | 230.52, 231.72 and 238.36 |
| H2O | OH | 281.13, 306.36 |
| NH3 | NH | |
| N2 | N2 | 337 (close to NH) |
| CO2, CO | CN | 388.34, 387.14, 386.19, 421.60, 359.04 |
| CH4, CnHm | CH (A > X) | 431.3 and lower wavelength rot. lines |
| CH3OH, CO | CO Angstrom Bands | 438, 450, 283, 519, 560, 608 |
| CH4, CnHm | C2 Swan Bands | 560 |
| CH2Cl2, CHCl3 | Cl+ | 481, 521.8, 543 |
| | Cl | 837.5, 858.6 |
| | H Balmer | H Balmer |
| O2 | O | 777.19, 777.414 and 777.543 |

*Figure 3*

| Table 1. Grating Spectrometer and PD-CCD Features | | | | | | | | |
|---|---|---|---|---|---|---|---|---|
| Blazing Order | g,Grating Const in nm | Focal Dist. μm | Grat Width W in μm | Pixel Size μm | Num. N = W/g | Grooves Resolution R=nxN | MDD in μm Image 11.31 | Wavelength's n = 1 |
| 2 | 850 | 1,000 | 200 | 6.8 | 235 | | 8 | λ |
| λ | sin(δ) | s in μm | Dispersion | Resolution | Angle | Δλ = λ/nN | Resolution | |
| nm | - | μm | nm/μm | nm/pixel | degrees | nm | nm | nm |
| 0 | 0 | 0 | 0.425 | 2.9 | 0.00 | 0.00 | 4.81 | 0 |
| 100 | 0.2352941 | 235.29 | 0.425 | 2.9 | 13.61 | 0.21 | 4.81 | 200 |
| 200 | 0.4705882 | 470.59 | 0.425 | 2.9 | 28.07 | 0.43 | 4.81 | 400 |
| 300 | 0.7058824 | 705.88 | 0.425 | 2.9 | 44.90 | 0.64 | 4.81 | 600 |
| 400 | 0.9411765 | 941.18 | 0.425 | 2.9 | 70.25 | 0.85 | 4.81 | 800 |
| 500 | 1.1764706 | 1176.47 | 0.425 | 2.9 | #NUM! | 1.06 | 4.81 | 1000 |
| 600 | 1.4117647 | 1411.76 | 0.425 | 2.9 | #NUM! | 1.28 | 4.81 | 1200 |
| 700 | 1.6470588 | 1647.06 | 0.425 | 2.9 | #NUM! | 1.49 | 4.81 | 1400 |

*Figure 4A*

Table 2. Grating Spectrometer and PD-CCD Features

| Blazing Order | g,Grating Const in nm | Focal Dist. μm | Grat Width W in μm | Wafer Th. μm | Num. Grooves N = W/g | Resolution R=nxN | MDD in μm Gap: 30.0 | Wavelength's n = 1 |
|---|---|---|---|---|---|---|---|---|
| 2 | 1341.6 | 7,500 | 1500 | 1500 | 1118 | | Image 42.43 | λ |
| λ nm | sin(δ) | s in μm μm | Dispersion nm/μm | | Angle degrees | Δλ = λ/nN nm | Resolution nm/pixel | nm |
| 0 | 0 | 0 | 0.0894 | | 0.00 | 0.00 | 3.79 | 0 |
| 100 | 0.1490712 | 1118.0 | 0.0894 | | 8.57 | 0.04 | 3.79 | 200 |
| 200 | 0.2981424 | 2236.1 | 0.0894 | | 17.35 | 0.09 | 3.79 | 400 |
| 300 | 0.4472136 | 3354.1 | 0.0894 | | 26.56 | 0.13 | 3.79 | 600 |
| 400 | 0.5962848 | 4472.1 | 0.0894 | | 36.60 | 0.18 | 3.79 | 800 |
| 500 | 0.745356 | 5590.2 | 0.0894 | | 48.19 | 0.22 | 3.79 | 1000 |
| 600 | 0.8944272 | 6708.2 | 0.0894 | | 63.43 | 0.27 | 3.79 | 1200 |
| 700 | 1.0434984 | 7826.2 | 0.0894 | | #NUM! | 0.31 | 3.79 | 1400 | g,Grating Const. in nm:1341.6  ;δ in deg for λ = 300nm:26.56

PD-CCD(400-200nm) in μm: 2236.1.; Aperture, A = W/f = 0.2

$f = g * p/(n\ \Delta\lambda) = 7500$

*Figure 4B*

| Table 3. Spectrometer for 200-400nm: Comparison of Design and Performance Parameters ||||||||
|---|---|---|---|---|---|---|---|
| Design | Order | Blaze An. | Gr.Const | Focal Dist. | Pixel size | λ-Resol. | Ph. Diodes | MDD Gap |
| - | - | deg. | µm | µm | µm | nm | - | µm |
| Fig.1 | 4 | 22.5 | 1.7 | 1,000 | 6.80 | ~4.8 | 69.0 | 8.0 |
| Fig.2 | 2 | 22.5 | 0.85 | 1,000 | 6.80 | 4.81 | 69.0 | 8.0 |
| Fig.3 | 2 | 13.28 | 1.34 | 7,500 | 42.43 | 3.79 | 52.7 | 30.0 |

*Figure 4C*

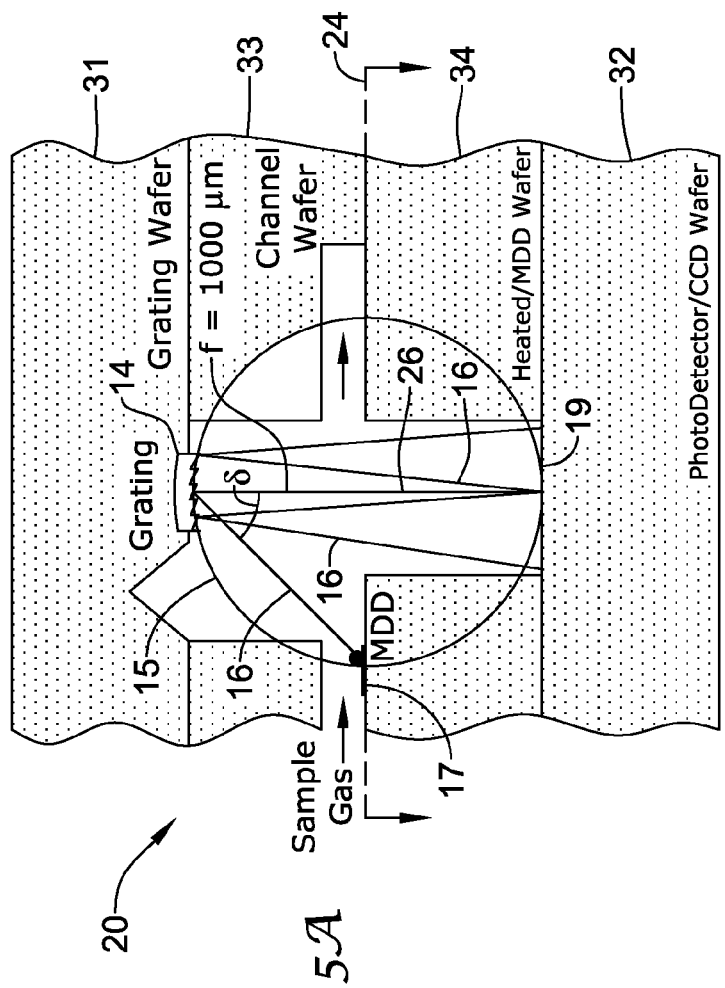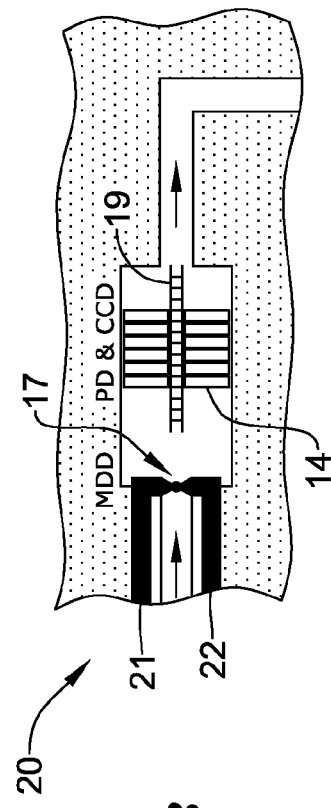
Figure 5A
Figure 5B

OPTICAL MICRO-SPECTROMETER

This application claims the benefit of U.S. Provisional Application No. 60/681,776, filed May 17, 2005. This application claims the benefit of U.S. Provisional Application No. 60/743,486, filed Mar. 15, 2006.

The U.S. Government may have some rights in the present invention.

BACKGROUND

The present invention pertains to spectrometers and particularly to micro spectrometers. More particularly, the invention pertains to micro spectrometers for fluid analyses.

U.S. patent application Ser. No. 11/383,728, filed May 16, 2006, entitled "Chemical Impedance Detectors for Fluid Analyzers," by U. Bonne et al., is hereby incorporated by reference. U.S. patent application Ser. No. 11/383,663, filed May 16, 2006, entitled "A Thermal Pump," by U. Bonne et al., is hereby incorporated by reference. U.S. patent application Ser. No. 11/383,650, filed May 16, 2006, entitled "Stationary Phase for a Micro Fluid Analyzer," by N. Iwamoto et al., is hereby incorporated by reference. U.S. patent application Ser. No. 11/383,738, filed May 16, 2006, entitled "A Three-Wafer Channel Structure for a Fluid Analyzer," by U. Bonne et al., is hereby incorporated by reference. U.S. Provisional Application No. 60/681,776, filed May 17, 2005, is hereby incorporated by reference. U.S. Provisional Application No. 60/743,486, filed Mar. 15, 2006, is hereby incorporated by reference. U.S. patent application Ser. No. 10/909,071, filed Jul. 30, 2004, is hereby incorporated by reference. U.S. Pat. No. 6,393,894, issued May 28, 2002, is hereby incorporated by reference. U.S. Pat. No. 6,837,118, issued Jan. 4, 2005, is hereby incorporated by reference. U.S. Pat. No. 7,000,452, issued Feb. 21, 2006, is hereby incorporated by reference. These applications and patents may disclose aspects of structures and processes related to fluid analyzers.

SUMMARY

The present invention is an optical micro spectrometer using a grating and compact light source, which is applicable to fluid composition analysis.

BRIEF DESCRIPTION OF THE DRAWING

FIG. 3 has a table of wavelength emission bands in the IR, visible and UV wavelengths for monitoring and quantifying certain components in combustion engine exhaust;

FIG. 4 shows tables with specifications for spectrometer designs;

FIGS. 5a and 5b are side cross section and top views another illustrative example of a multi-wafer spectrometer;

DESCRIPTION

Figure 1:
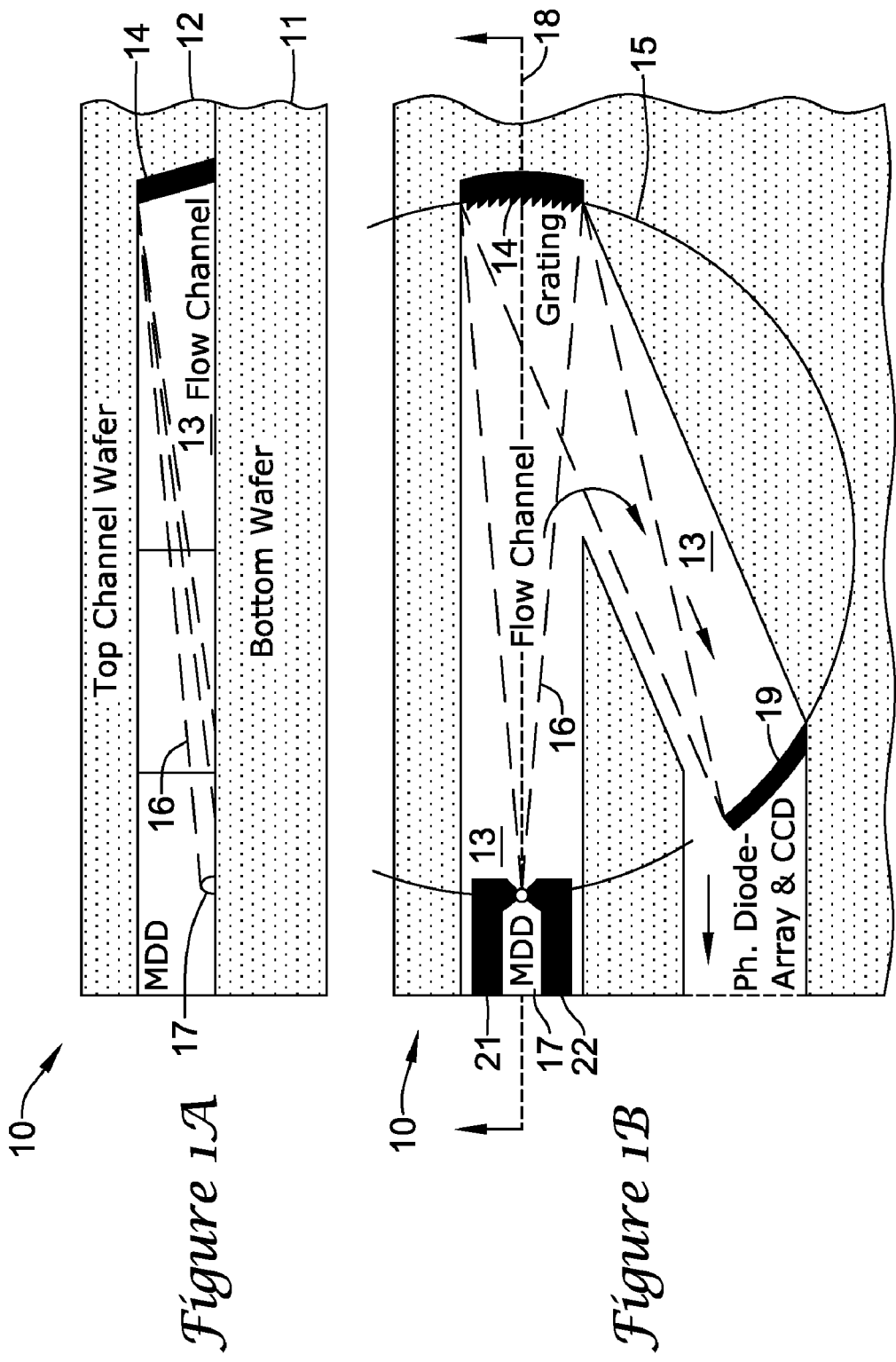
FIGS. 1a and 1b show an edge view and a top view of an illustrative example of a multi-wafer spectrometer.

FIGS. 1a and 1b show an edge view and a top view of a two wafer spectrometer, device or configuration 10. FIG. 1a is a cross section at a line 18 of the spectrometer or device 10 in FIG. 1b. A bottom wafer 11 is a substrate with the top wafer 12 situated on it. The top wafer 12 has a flow channel 13. The spectrometer may be based on a concave diffraction grating 14 or other similar wavelength sensitive reflective mechanism, mounted proximate to a circle 15, such as a classic Rowland circle. A light 16 may be emitted by a light source 17 such as a micro discharge device (MDD). The light 16 may proceed through a portion of the flow channel 13 to a grating 14. Grating 14 may reflect the light 16 at an angle down another portion of the flow channel 13 towards a photodiode array and/or CCD detector 19. The detector may be an array. Light source 17 and detector 19 may be situated proximate to the Rowland circle 15. So the light path may go from source 17 to grating 14 and from grating 14 to detector 19. All three items 17, 14 and 19 may be situated near or on circle 15.

The grating or reflector 14 may be a concave diffraction grating, a holographic concave reflective grating, or a focusing transmission grating. Source 17 may be a micro discharge device or a bright surface reflection from a laser focused onto that surface.

Figure 2:
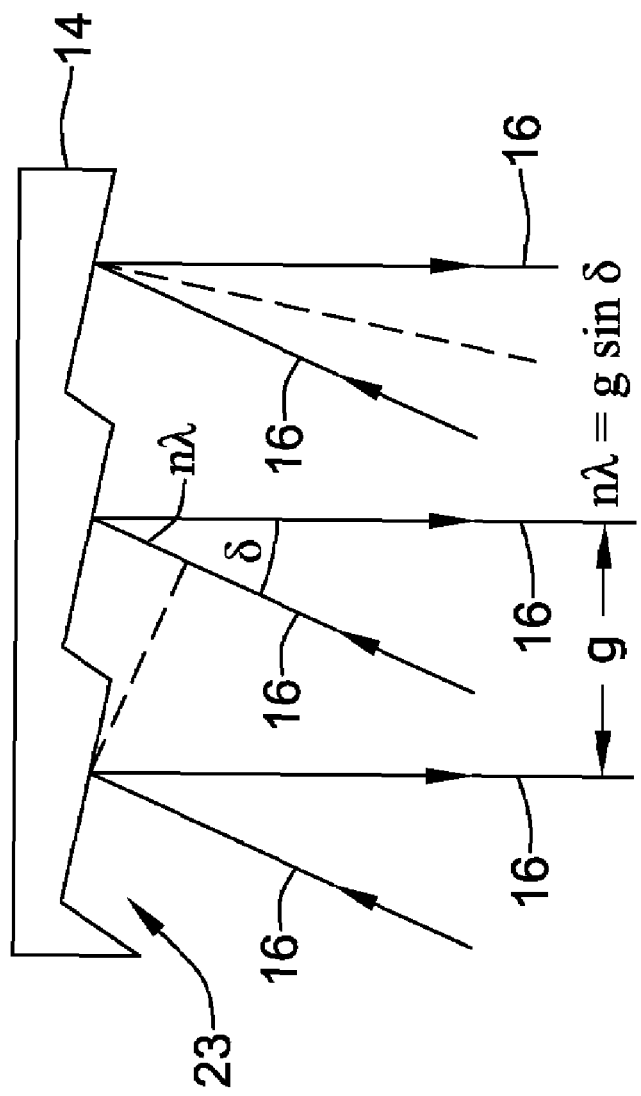
FIG. 2 shows an example of a grating used in a small spectrometer.

The location of a particular wavelength $\lambda$ on the Rowland circle may be give by the equation $n\lambda = d(\sin \theta + \sin \delta)$, where n is the order, g is the grating spacing, $\theta$ is the angle of incidence of light on the grating and $\delta$ is the angle of reflection off the grating. If the angle of incidence is zero, then the equation may be $n\lambda = g \cdot \sin \delta$. FIG. 2 illustrates an example grating 14, grooves 23, incidence and reflected light 16, and some related parameters.

A characteristic of the spectrometer 10 may reside in its wafer-level (11, 12) manufacture (wafer of gratings and wafer of photo-detector arrays 19 (image intensifier arrays, CCDs or charge-injection detectors (CIDs)), which would be compatible with a fluid analyzer, such as a phased heater array structure for enhanced detection (PHASED) micro gas analyzer (MGA). The spectrometer 10 may provide excellent compactness (1-60 mm$^3$), affordability, flexibility and response speeds than possible with interference filters or commercial mini-spectrometers to process spectro-chemical emission from a micro discharge device (MDD) 17. The term "fluid" may refer to a gas or a liquid, or both.

This invention may provide clear analytical-capability advantages to PHASED, μRaman, MDD-based $NO_x/O_2/NH_3/SO_2$ sensors, and other like sensors, and other applications of MDDs 17 in industry and government to monitor concentrations of Cl—, F—, P—, Hg—, Cd—, and so on, containing compounds with specific MDLs in the ppb-ppm range. Presently available analyses of micro discharge device (MDD) 17 optical emissions may require either a number of discrete, narrow band-pass optical filters, poorly-reproducible sliding transmission band-pass filters, or costly and complex chip-level, but still relatively bulky, optical spectrometers. None appears to lend itself to easy integration into $NO_x$ sensors or PHASED MGAs based on MDDs.

The spectrometer of the present invention may leverage available sample gas flow channels in $NO_x$ sensors or in wafer-to-wafer bonded MEMS (micromachined electro mechanical system) structures such as PHASED MGAs to support an MDD light source 17, a single reflective surface (grating) 14, and an array 19 of photo detectors (diodes or transistors) coupled to a CCD array. It may support a reasonable numerical aperture of 1/5 and feature a standard CCD output, with spectral resolutions below 5 nm/pixel. The invention make fabrication possible including micromachining (i.e., etching) a set of grating grooves 14 with a grating constant of 0.250-1 μm and having the photo detector-CCD array 19 on the same chip 11, 12 as the MDD 17 electrodes 21 and 22. The spectrometer 10 may be viewed as a functional, low-cost MDD 17 sensor of $NO_x$—$O_2$—$NH_3$—$CO_2$—$SO_2$ for combustion exhaust (automotive and stationary) as well as a detector for the PHASED micro gas analyzer.

One may provide multiple detector channels for 5-10 wavelength bands via discrete interference filters deposited at the ends of polished optical fibers or on individual photodiodes. This may be an alternative of a low-cost spectrometer. Small, pocket size spectrometers and chip-level spectrometers may be available. However, a related-art "integrated" spectrometer may need a CCD camera placed at a distance of 35 cm from the MDD.

A related-art grating spectrometer may have a resolution of 3 pixels/nm but not a known good dispersion (in nm/μm). Other features and requirements that are to be achieved with the present device may include, for example, a large aperture to maximize S/N. Spectral resolution may be $\Delta\lambda \leq 5$ nm half-width, so that $\lambda/\Delta\lambda \geq 300/5=60$. There may be a sufficient number of grating grooves, N, (in grating 14) to achieve a $\lambda/\Delta\lambda \leq n \cdot N$ resolution that is greater than the one given by the image of the slit+MDD+optical fiber on the CCD pixels, where n is the order of the observed grating spectrum. Blazing of the grooves may be consistent with the desired observation order. Observation order and spectral- and detector-range may be provided to minimize interference among different orders at the detector array 19. There may be diffraction-limited resolution and focusing on the PDs (photo diodes). The overall small overall volume may enable wafer-level, high-volume and low-cost fabrication. Detection of spectral MDD emission may be in the 200-400 nm range.

A grating spectrometer may have a resolution of 3 pixels/nm (nm may be used to designate the dimension of the used wavelength, while mm may be for the spatial dimension of the detector array) but not a known good dispersion (in nm/mm). Other items that may be achieved with the present device may include, for example, a large aperture to maximize S/N. Spectral resolution may be D1*5 nm half-width, so that 1/D1*300/5=60. There may be a sufficient number of grating grooves, N, (in grating 14) to achieve a 1/D1*n*N resolution (where n=grating dispersion order), that is greater than the one given by the image of the slit+MDD+optical fiber on the CCD pixels, where n is the order of the observed grating spectrum.

Sources of cameras and PD (photo diode) arrays with CCDs for detector 19 may include a Kodak KAF1401E CCD camera with pixel size 6.8 μm, Sony DXC-107 CCD Camera with 768×494 pixels of 8×9.5 μm, Marconi CCD37 camera with pixels of 15.0 μm, and a CCD by E2V Technologies model CCD38-20, having 44 μm square pixels and a 456×684 μm pixel image area with a 100 μm thick Gadox (Gd2O2S) scintillator.

An approach taken to achieve satisfactory operation and satisfy the requirements listed above may be illustrated in FIGS. 1a, 1b, 5a, 5b, 6 and 9. FIGS. 1a and 1b show the feasibility of fabricating a spectrometer within the two-wafer (11, 12) structure of PHASED. FIG. 5a is side view of a spectrometer, device or configuration 20 with a top view at about line 24 shown in FIG. 5b, including views of the grating 14 and detector 19. A feature is the integration of the fabrication of sub-micron, smooth and concave grating grooves (via DRIE into the grating wafer 31) and the PD-CCD array (photo-detector-charge-coupled device) 19 into the wafer 32. The dimensions of device 20 may stay within an acceptable 1×1×1 mm volume, assuming that the size of the MDD source 17 ($\leq$electrode (21, 22) gap=8 μm) and its image on the PD-CCD array (11.3 μm) 19 are small enough to achieve the desired resolution.

FIGS. 5a and 5b show a solution the integration challenge by allowing for separate wafers 31 and 32 to hold the grating 14 with its grooves 23 and concave surface, and the PD-CCD array 19, respectively.

Bonding a stack with a greater number of wafers, including wafers 33 and 34 as the channel wafer and the heater wafer, respectively, along with grating wafer 31 and detector wafer 32, is one approach for integrating a small-sized spectrometer into an MGA. The volume requirements of device 20 appear to be similar to those of device 10 shown in FIGS. 1a and 1b, again assuming that the size of the MDD source ($\leq$electrode gap=8 μm) and its image on the PD-CCD array (11.3 μm) are small enough to achieve the desired resolution. The focal distance 26 between grating 14 and detector or receptor 19 may be about 1000 microns.

Figure 6:
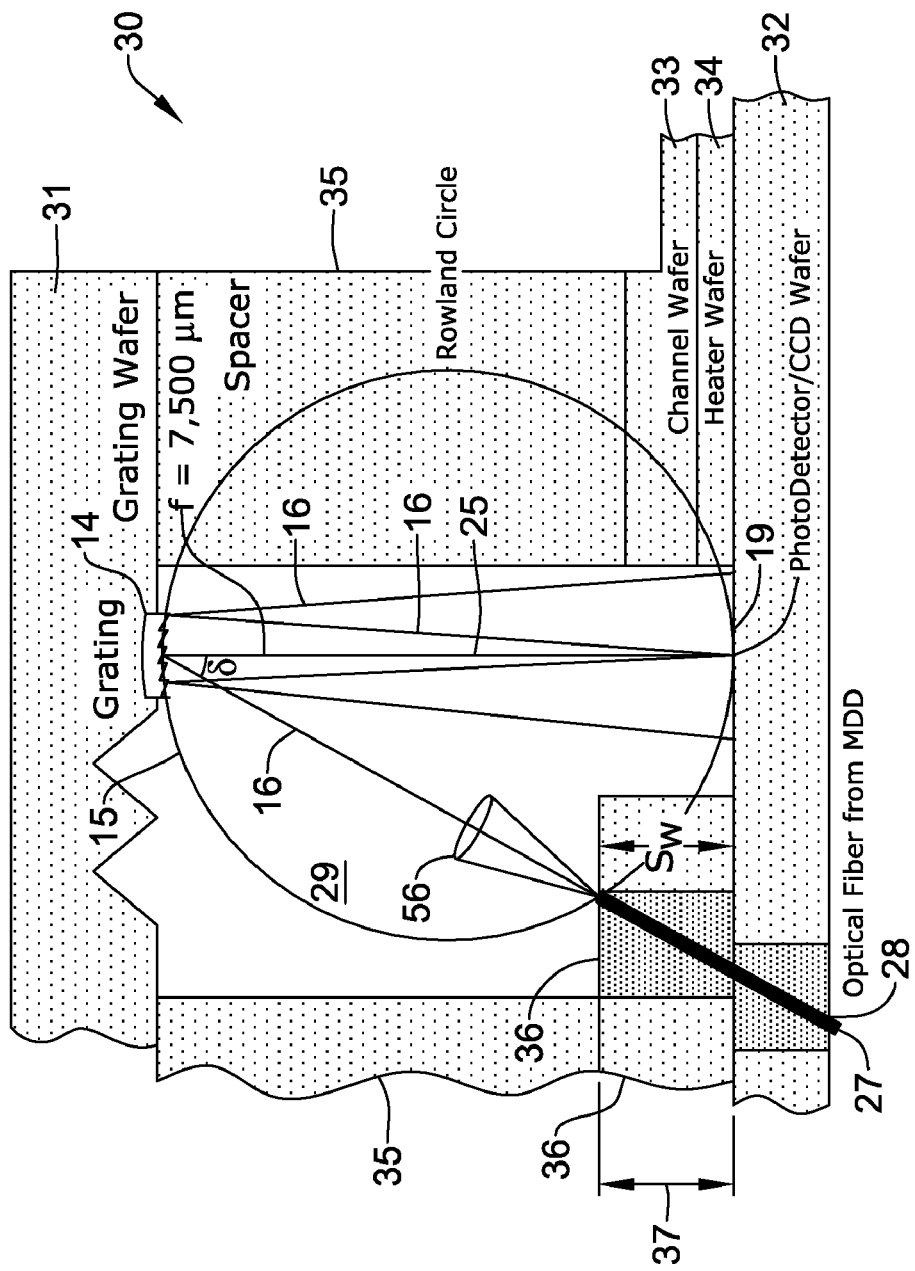
FIG. 6 is a cross section side view of an illustrative example of a spectrometer with an external light source.

FIG. 6 may preserve the configuration of FIGS. 5a and 5b with a spectrometer, device or configuration 30 to allow separate fabrication of grating 14 and PD-CCD 19, and additionally overcome the MDD 17 size limitation, which may be relaxed to a 30 μm size gap, resulting in a 42.43 μm image size and a grating-to-PD-CCD array distance 25 of f ~=7500 μm (7.5 mm). The overall volumetric size may be increased from the herein noted ~1 $mm^3$ to ~18 $mm^3$. The main geometrical/fabrication difference between the devices 20 and 30 represented in FIGS. 5a and 6 may be the extra "spacer wafer" 35, between the "grating" and the "channel wafers" 31 and 33, respectively, in FIG. 6. The "spacer" 35 in FIG. 6 may have a thickness of about 6 mm on top of the wafer 36 that supports the MDD or light source 17, which may have a thickness 37 of $s_w$=1.5 mm. Layer 35 may also be situated on the channel wafer 33 can be on a heater wafer 34. Wafers 33 and 34 may together have about the same thickness as wafer 36.

From a set of specific characteristics, one may derive the following general step-by-step guidelines for the making of the subject low-cost spectrometer 10, 20 and/or 30, as illustrated by specifications in the first table of FIG. 4, with inputs encompassed by dashed boxes. An initial step may be scaling. Here, one may determine the image or focal distance d (25, 26) between the grating 14 and the PD-CCD array 19 (and as provided by the diameter of the Rowland Circle 15), equating the dispersion $D_i$, (needed for the finite image of the light source to achieve the desired spectral resolution, $\Delta\lambda$), with that generated by the grating, $D_g$. $D_i$ may be governed by geometrical optics of imaging the source (slit or MDD 17) onto the PD-CCD array 19 of total length $p \cdot N_p$, to cover the λ-range $\lambda_2 - \lambda_1$:

$$D_i = (\lambda_2 - \lambda_1)/p \cdot N_p = (\lambda_2 - \lambda_1)/\{p \cdot (\lambda_2 - \lambda_1)/\Delta\lambda\} = \Delta\lambda/p,$$

where $N_p = (\lambda_2 - \lambda_1)/\Delta\lambda = (400-200)/3 = 200/3 = 67$; and p=pixel size in μm. On the other hand, $D_g$ may be given by the grating groove width, g, the spectral order, n, the diffraction angle, δ, and the focal distance, f:

$$D_g = (\lambda_2 - \lambda_1)/(s_2 - s_1) = (\lambda_2 - \lambda_1)/\{f(\sin \delta_2 - \sin \delta_1)\} = g/(f \cdot n)$$

where $s_{1,2}$=distances on the PD-CCD array 19 focal plane corresponding to the wavelengths $\lambda_{1,2}$, and $\sin \delta_{1,2} = n \cdot \lambda_{1,2}/g$.

Therefore, with g=1342 nm, p=42.4 μm, n=2 and Δλ=3.79 nm, one may achieve, $$f \geq g \cdot p/n \cdot \Delta\lambda = 7500 \text{ μm}.$$

The next step may be the grating 14. Fabrication of the grating grooves 23 spaced at g=850 nm (see the first table in FIG. 4) may tax fabrication capabilities. To ease fabrication of wider grooves 23, the second table in FIG. 4 is based on g=1342 nm, which may result in a focal distance of f=7500 μm as shown herein.

An additional step may be a blazing of the grooves 23 consistent with the desired observation order. For the devices 10 and 20 of FIGS. 1a, 1b, 5a and 5b, this may mean an angle of 45/2=22.5°. For the device 30 of FIG. 6, the blazing angle may have to be δ/2=13.3°.

A further step may be the aperture. Considering the center incident beam 16 to the grating 14, the aperture may be A=(g·N/√2)/(f/√2)=g·N/f. For the device 30 of FIG. 6, to achieve A=1/5, it may be required that N=A·f/g=(1/5)·7500/1=1,118 grooves.

Another step may be the diffraction-limited resolution and focusing on the PDs 19. One may achieve this by checking that the diffraction limit given by $L_d$=0.61·λ/A=915 nm=0.915 μm, does not exceed the optical resolution or definition of the present PD-CCD array 19, which may be represented by the pixel size, 11≦p≦43 μm, to cover the resolution range from that in FIGS. 1a, 1b, 5a and 5b to that of FIG. 6.

A subsequent step may be separation of grating orders. By observing the 200-400 nm MDD emission spectrum at the $2^{nd}$ order (n=2), one may also cover the 777 nm O-lines in the $1^{st}$ order, provided that the two are kept apart, which one may do by covering the PD-CCD pixels for the 777 nm lines with a UV-blocking filter such as glass, so that the complete spectrometer detection range does not need to be extended to ~800 nm in the second order.

A process for a making of the device 30 in FIG. 6 may be modified to enable input the desired aperture and the MDD 17 position (up from the PD-CCD 32 wafer in μm and on the Rowland circle 15) and is captured in the second table in FIG. 4, with inputs highlighted with dashed-line boxes. One may input aperture and distance 25 between grating 14 and PD-CCD array 19, f, and calculate W. One may input the MDD-support wafer 36 thickness 37, $s_w$, and calculate the diffraction angle, δ, and wavelength positions on the PD-CCD array 19, s, and the corresponding dispersion in nm/μm. One may input the MDD 17 gap size and calculate the MDD image size (assumed to be equivalent to one pixel) and the spectral resolution in nm/pixel. If the latter is larger than the desired 3-5 nm/pixel, one may adjust f, $s_w$, and/or the MDD gap, until the desired resolution is achieved.

There may be assembly and operation of the micro-spectrometers 10, 20 and 30. The assembly may be shown by FIGS. 1a, 1b, 5a, 5b and 6. An attachment of an optical fiber 27 carrying the optical emission from an MDD 17, at a remote location, e.g., exposed to sample gases from a harsh car exhaust at that remote location, may need to be carefully made. Such a fiber 27 may be made to end at nearly exactly the same point at which FIGS. 1a, 1b, 5a, 5b and 6 show the MDD 17 gap, through as many wafer thicknesses as needed, preferably at an angle that points to the center of the grating 14. If a hole 28 is etched that is larger than the optical fiber 27, fastening and sealing the fiber 27 at such an angle may be possible due to the extra dead-space. The use of such an optical fiber 27 may be better than having the sample gases enter the grating cavity 29, in order to maintain long term, maintenance-free operation.

There may be a need to align the spectrometer elements relative to one another, such as the light source (MDD) 17, grating 14 and PD-CCD array 19. During operation, the MDD-source 17 may be ultimately imaged on the PD-CCD array 19. The outputs of array 19 may then be further processed (i.e., amplified, digitized, integrated and displayed) as needed.

Figure 7:
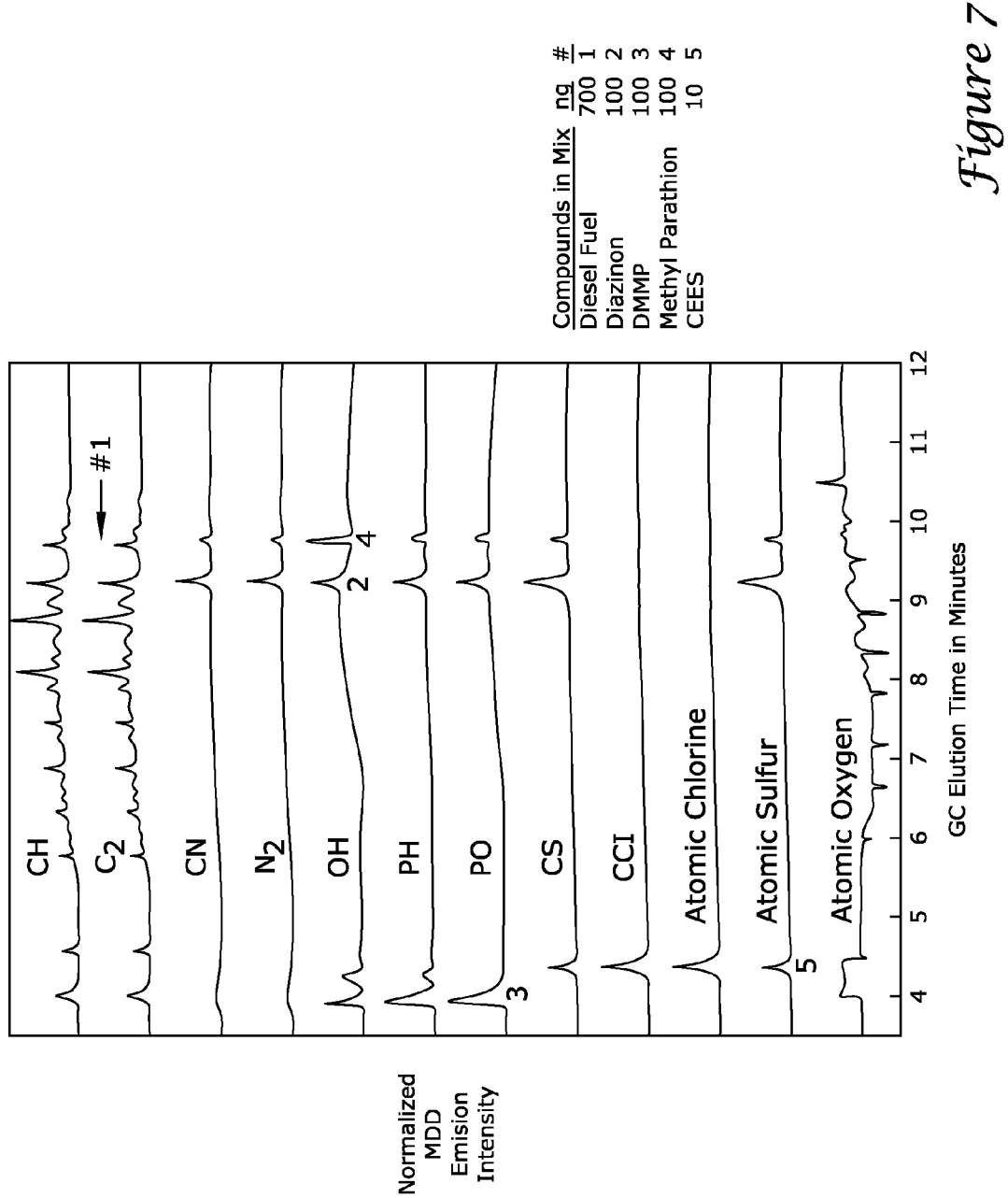
FIG. 7 shows a graph of general chromatography elution times of various simulants.

Some recommended wavelength bands for monitoring and quantifying $NO_x$, $O_2$, $SO_2$, $NH_3$, $CO_2$, and $H_2O$ in combustion engine exhaust are listed in a table in FIG. 3. The detection of CWA (chemical warfare agent) simulants with gas chromatography (GC) or PHASED MGA with, for instance, an Ocean Optics Co. spectrometer, used as indicated here is illustrated in FIG. 7. The graph of FIG. 7 shows GC elution times in minutes of various simulants. The MDD outputs shown in FIG. 7 are for a chromatogram of diesel fuel with CWA simulants, at twelve wavelengths.

The ~2×3×4" size of the Ocean Optics spectrometer may represent the state-of-the-art of commercial spectrometers, which is not large relative to desk-top conventional units, but is rather large relative to the size of the present devices 10, 20 and 30.

As mentioned herein, and in order to observe the 777 nm lines of O (representing $O_2$ concentration) without having to extend the wavelength range in the $2^{nd}$ order to 777 nm, one could place a UV-blocking filter such as glass on the pixels corresponding to the $2^{nd}$ order range of 77/2=388.5±2 nm. Conversely, broad filters blocking the 400-800 nm of the $1^{st}$ order may reduce potential interferences between the two orders.

To minimize light scattering, suitable light-absorbing coatings may be applied to the walls of the channel or column, and consideration be given to place light-stopping blends, although a coating consisting of carbon nanotube (CNT) grass may obviate this need.

In the fabrication of the present device, the specifications noted here may be for a differential MDD 17 design in a 100×100 micron channel, to operate in air, and be duty-cycled as much as possible but able to follow GC peaks of >15 ms half-width. Measurements may include MDD impedance, current or voltage and an optical output into 3-8 channels selected via interference filters.

One may attain a glass wafer, such as Pyrex™ (to host the PHASED channels), which might also support MDD 17 electrodes 21 and 22 and transmit MDD light 16 through it (poorly in UV but acceptable in visible light). A small "interference gradient" filter may be placed on the outside surface of the glass wafer, with a small-pitch photo-CCD or channeltron array situated on top of the CCD or array 19. One may obtain the wafer, put the channels into it and provide the optics. The glass thickness at the MDD 17 may be thin. One may "seal" the MDD electrodes 21 and 22 into the glass with a thick dielectric coating applied on the optical output side, so that the plasma does not light up on the detector side.

Figure 8A:
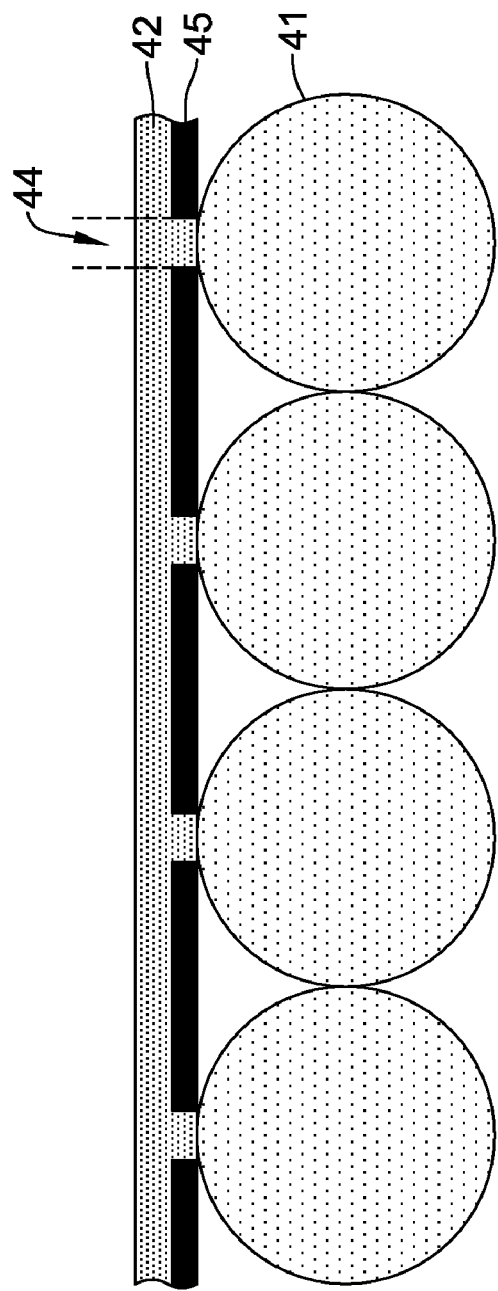
FIGS. 8a and 8b show cross-sectional views of an approach for fabricating concave gratings.
Figure 8B:
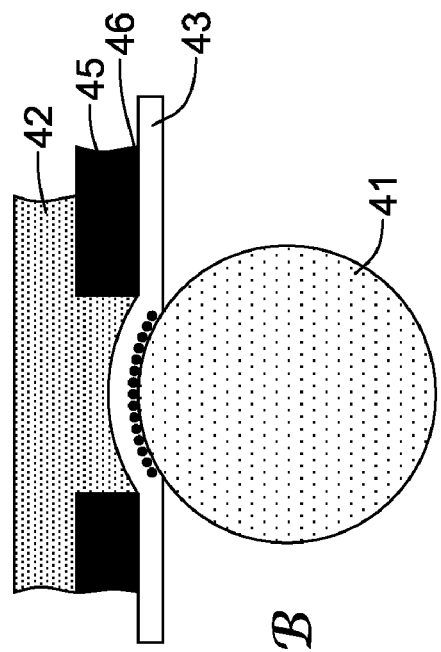

FIGS. 8a and 8b show cross-sectional views of a fabrication of a concave micro grating array 14. FIG. 8a may be approximately to scale and FIG. 8b may have an enlarged view of a preformed epoxy 42 and a shaping of a film or membrane 43 for the grating 14. A spherical surface shape may be made with a hard surface 41 (a stainless ball bearing) pressing into a soft surface 42 (epoxy), and then shaping the membrane 43 over the "dimple" made by the ball bearing 41. The grating 14 may be written on the membrane 43 surface while it is still flat. Then the membrane 43 may be formed into the dimple (possibly with air pressure). In this approach, one may have to eliminate the air behind the membrane 43 through some vent pore or porous surface, possibly in the epoxy 42. The membrane 43 may be attached to the silicon wafer 45 with an adhesive 46.

The "grated" film 43 should be deformed without squashing the grating grooves. One may, for example, press 7.5 mm OD ball-bearings 41 onto the deformable film 43). This may be an alternative to the use of pressure (which requires an extra fixture), since the pressing of a bearing 41 onto the film 43 provides a sure shot at getting the right spherical curvature. As to material, one may place a free $Si_3N_4$ membrane 43 over an array of 1.5-2 mm ID holes 44 in a Si wafer 45, which can be marked holographically on a photoresist, and etched with the grating grooves while in the "flat" state before being deformed by pressure. The deformation "depth" of that spherical shell of about 1.5 mm OD, with a 3.75 radius of curvature may be:

$$3.75-(3.75^2-0.75^2)^{0.5}=0.07576 \text{ mm},$$

or 76 microns in the middle of 1500 microns. This may correspond to a strain of $3.75*(\arcsin(0.75/3.75)-0.75)/0.75=0.0067896$, i.e., 0.679% and below the break point. The nitride fracture strength=$5.87\pm0.62$ GPa and Young's modulus=$255\pm5$ GPa, which indicates that the yield strain is 1.12%. Although the grooves may "initiate" fracture before 1.12% or even before 0.679%.

The grating 14 membrane may mimic the master grating (but in an inverted fashion). So if the master is blazed to a particular angle, so will be the duplicate be blazed as such. One may determine what type of lift-off film should be used, and how much the liftoff would tend to planarize the grating surface. However, even the first tries may be blazed the same as the master grating. Along with an epoxy 42, one may use a thermal deformation process to create the spherical shape, and then cool it to maintain the shape.

As part of the fabrication process, the thin membrane 43 may be deformed into a spherical shape (like a soap bubble) under gas or liquid pressure on one side, and an epoxy 42 on the other, which would solidify when one wants it, and then be bonded to the membrane (without deformation as it hardens).

The present device or micro-spectrometer 10, 20, 30 may reside in the design and its guidelines. The device may have truly integrated optics with an MDD light source 17, sealed optics (with the MDD operating in a sample gas stream and sending its emission via an optical "fiber", e.g., fiber 27, to a sealed optical device), a concave grating 14 and an array 19 of photo-detectors (PD-CCD). Optics 56 may facilitate the light movement within the device 30. The device may have wafer-level assembly and very extreme compactness (1-60 mm$^3$), but also low-cost of fabrication, by virtue of merging an independent, SOA fabrication of gratings 14 and of PD-CCD arrays 19. The device may meet the resolution needs for MDD 17 emission spectroscopy and provide a large optical aperture for a high signal/noise ratio and at high-speed (low integration time requirements) detection/measurements. The device may be fabricated with processes for the grating 14, MDD 17 and photo-detector arrays 19. It may use CNT grass as a very effective optical anti-reflector on spectrometer walls to minimize scattered light.

The emission spectrometer 10, 20, 30 may have great ruggedness reliability resulting from the presently noted fabrication and size features. This spectrometer may have very short response time (short signal integration time need) and a high S/N, due to large aperture of 1/5. The present spectrometer may have greater reliability and a higher S/N than the interference-filter-based approaches, due to the filter's center wavelength shift with temperature and incident angle, and an attempted cure of the latter by limiting the angle of incidence may reduce the light input and S/N.

There may be easy coupling between one or more optical fibers 27 (carrying the MDD 17 output) into the sealed microspectrometer, where the end(s) of the fibers function as a "point" or "slit" light source (see FIG. 6). The spectrometer may achieve better S/N due to use of CNT grass on internal surfaces to minimize noise caused by scattered light.

An issue that may be contended with is that the related art compact MGAs (micro gas analyzers) or fluid composition analyzers either require sophisticated, high-speed data processing to output species concentrations and use of energy-consuming pumps to transport and/or thin-out sample gas (required for micro mass spectrometers and micro gas chromatographs), and/or exclude a host of gases of interest such as $O_2$, $N_2$ and $H_2$ (as with IR or NDIR analyzers), and/or are too unstable to reliably serve in critical industrial processing or safety-related applications (polymer and SAW sensors; and MOS and electrochemical gas sensors, of which some are intrinsically un-safe by requiring $\geq 300°$ C. for operation).

Figure 9:
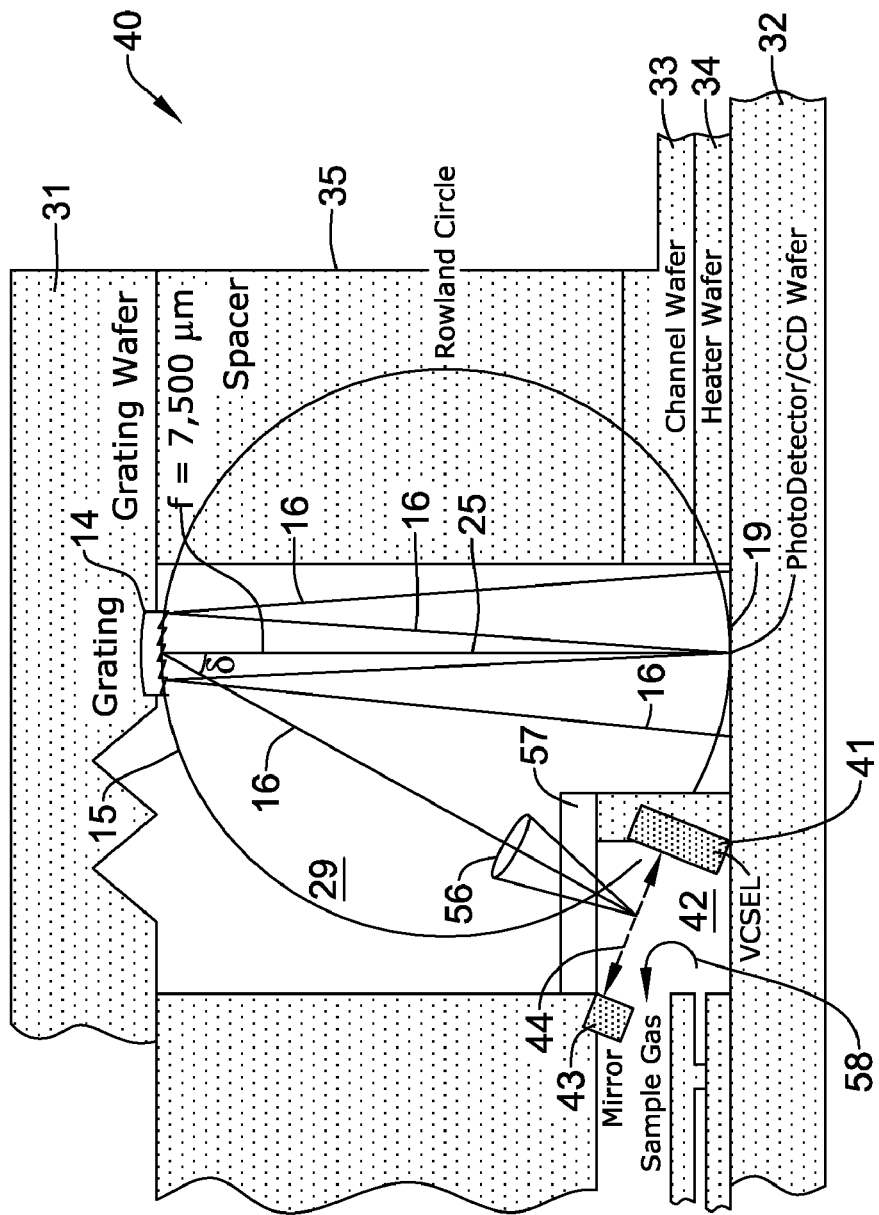
FIG. 9 shows an illustrative example of a micro Ramam spectrometer.

A fluid composition micro-analyzer 40 of FIG. 9 may leverage the Raman scattering signature that each component of a mixture provides without regard to its molecular symmetry (so that symmetrical zero-dipole gases such as $O_2$, $N_2$ and $H_2$ are not excluded), and the availability of chip-level, low-cost lasers (VCSELs) as light sources. Also, may leverage the possibility of increasing the aperture of the photo-detectors and thus the optical efficiency and minimum detection limit (MDL) of the whole MGA by using a (chip-level) micro spectrometer rather than a limited number of individual, rigid and fixed wavelength detectors behind small aperture and lossy interference filters.

The principle of the spectrometer 40 may involve a micro Raman scattering fluid analyzer, coupled to a μspectrometer with possible coupling to a PHASED MGA. Aspects of the present spectrometer 40 may include a micro Raman gas or liquid analyzer of revolutionary compactness, high aperture and thus high S/N and low MDL, short response time, and low-power consumption. The lasing cavity beam may operate as an entrance slit light source into a sealed μspectrometer (after turning the image in FIG. 9 by 90°).

The capability for the Raman spectrometer 40 to simultaneously sense $O_2$, CO, $CO_2$, NO and $NO_2$, coupled to its low cost, may make this device useful for internal and external combustion applications, besides its use in medical, industrial and government applications.

As stated herein, GC-MS analyzers may require significant data processing to identify and quantify the one or more analytes present in an unknown sample gas. Especially computation-intensive may be analyte mixtures, which consume time and electric power. Such computing power needs might not be much reduced with IR absorption analyzers, especially with analyte gas mixtures.

However, overwhelming computing requirements to identify and quantify analytes are not necessarily needed with Raman spectroscopy, because Raman scattering spectra appear much simpler than the signatures of GC-MS or IR analyzers, except possibly the simple NDIR analyzers with just a few (and therefore less reliable) wavelength-band channels.

Figure 10:
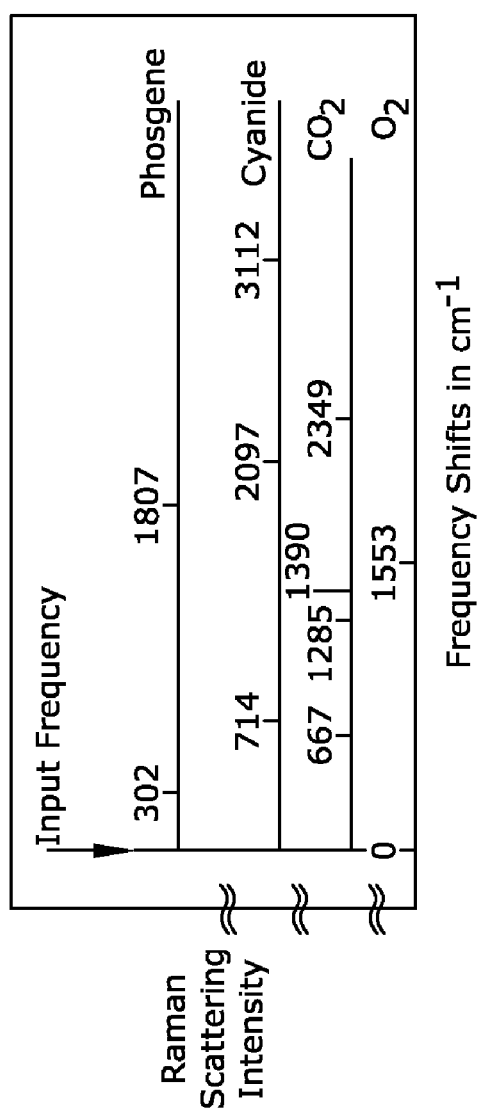
FIG. 10 shows a graph of some Raman spectra lines.

The simplicity of Raman scattering spectra is illustrated with the few Raman lines graphed in FIG. 10, which are in units of cm$^{-1}$, for phosgene, $CO_2$, cyanide and $O_2$. The plot in FIG. 10 shows a material versus an increasing Raman frequency shift of the scattered-light output, relative to the frequency of the input light. Measurement of this shift appears easier to achieve with low-resolution ($\lambda/\Delta\lambda$) in the IR than in the visible or UV, although the scattering intensity or efficiency may be higher at shorter wavelengths. Besides the scarcity of lines compared to an IR spectrum or even the mass fragments of a MS (mass spectrometer) signature, another striking feature seems to be the capability to select the wavelength region of operation by choosing the input laser wavelength, of which the resulting and plotted Raman shifts are not dependent on. More complex molecules may have a few more lines than simpler ones. Furthermore, FIG. 10 shows that diatomic molecules such as $O_2$ (or $H_2$, $N_2$) may have well-defined and observable line shifts, which spectrometry in the near IR would not provide.

The application of these fundamental aspects of Raman spectro-meters may be hindered by the presently available and relatively bulky and not portable Raman MGA versions. The present spectrometer 40 may reveal how to micro-miniaturize as well as increase the functionality of known Raman spectrometers on several levels, besides size reduction. One part of the present spectrometer 40 may include using an optical detector 19 that is more versatile than the few optical bands defined by discrete optical narrow-band-pass filters used in the related art. FIG. 9 shows one version of a Raman spectrometer 40, in which the detector 19 may provide compactness, a 10-50 times increase in the number of optical detection channels relative to the related art, and a very high numerical aperture or f-number. The photo-detectors on the CCD array 19 may enable advantageous signal integration and processing. A VCSEL (vertical-cavity surface-emitting laser) light source 41 may be much more compact than gas lasers. To maximize service life, the sample gases do not come in contact (avoiding the risk of optical surface contamination) with the grating 14 of spectrometer 40, since there may be a window 57 between the light cavity 42 where the light source 41 and its mirror 43 are situated. However, the sample 58 may enter the external laser cavity 42 and interact with the light 44 for maximum Raman scattering output light 16. The heart of the Raman MGA spectrometer 40 may be the laser cavity 42. Especially, by the positioning of an external VCSEL 41-to-mirror 43 multi-reflection beam 44, which is not quite positioned as shown (but it is positioned as such for illustrative purposes) in FIG. 9, but beam 44 may be parallel to the grating 14 grooves 23. This configuration of device 40 may increase the S/N by at least another factor of 10, which in turn may increase the MDL by an equivalent amount. The Raman (scattered) light may then be generated from a line that is positioned as if it were the entrance slit of a spectrometer, and imaged onto similar shaped elements of the CCD photo-detector array 19 (unless provided with an appropriate cylindrical lens to focus the image line down to a "point", i.e., to a CCD array 19 of point-shaped detectors). The present Raman spectrometer 40 may be compatible with the sample gas outputs of pre-concentrated and component-separated analytes provided by a PHASED MGA via micro channels of about 100 μm ID.

Aspects of the present micro Raman (gas or liquid) spectrometer 40 may be combined with an MGA to result in a compact micro Raman analyzer using compact VCSEL light source 41 technology. The spectrometer use photo detectors 19 with a CCD array for optical detection, integration and a step of signal processing.

The advantages of the present micro Raman spectrometer 40 over the related art may include a 10-20 times reduction of reduced outer package dimensions (1000-8000 times in volume and weight reduction) and it may use an optical detector that is more versatile than the few optical bands defined by discrete optical narrow-band-pass filters. Also, the spectrometer 40 may have a 10-50 times increase in the number of optical detection channels relative to the related art. The present spectrometer 40 may have a very high (about 1/10) numerical aperture or f-number (coupled with a line-shaped scattering source) which may increase the S/N and cannot be used with narrow-band-pass interference filters because of their angular sensitivity (the passed wavelength is dependent on the angle of incidence). The high aperture of the present analyzer 40 may enable shorter integration time and thus overall faster total response time.

Figure 11:
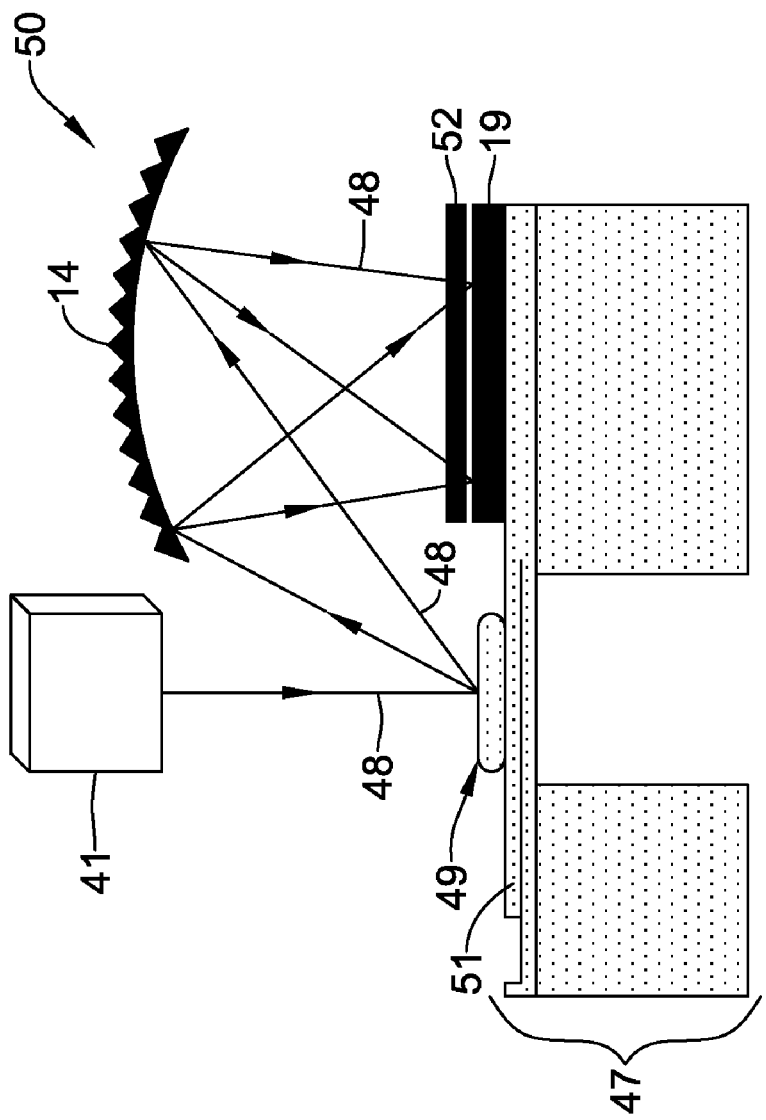
FIGS. 11 and 12 show illustrative examples of a surface-enhanced Raman spectrometer.

FIG. 11 shows an illustrative example of a surface-enhanced Raman spectrometer, configuration or device 50 relative to a PHASED detector structure 47. A VCSEL light source 41 may emit a light beam 48 which impinges a film 49 situated on a PHASED heater membrane 51 and is reflected to a grating 14. Grating 14 may reflect light 48, in part, through a notch or edge filter 52 to be detected by a micro CCD array 19. The film 49 may be regarded as a surface-enhanced Raman spectrometer film. The source of light may be for providing Raman scattering from a fluid adsorbed on the film-surface illuminated by the light.

Figure 12:
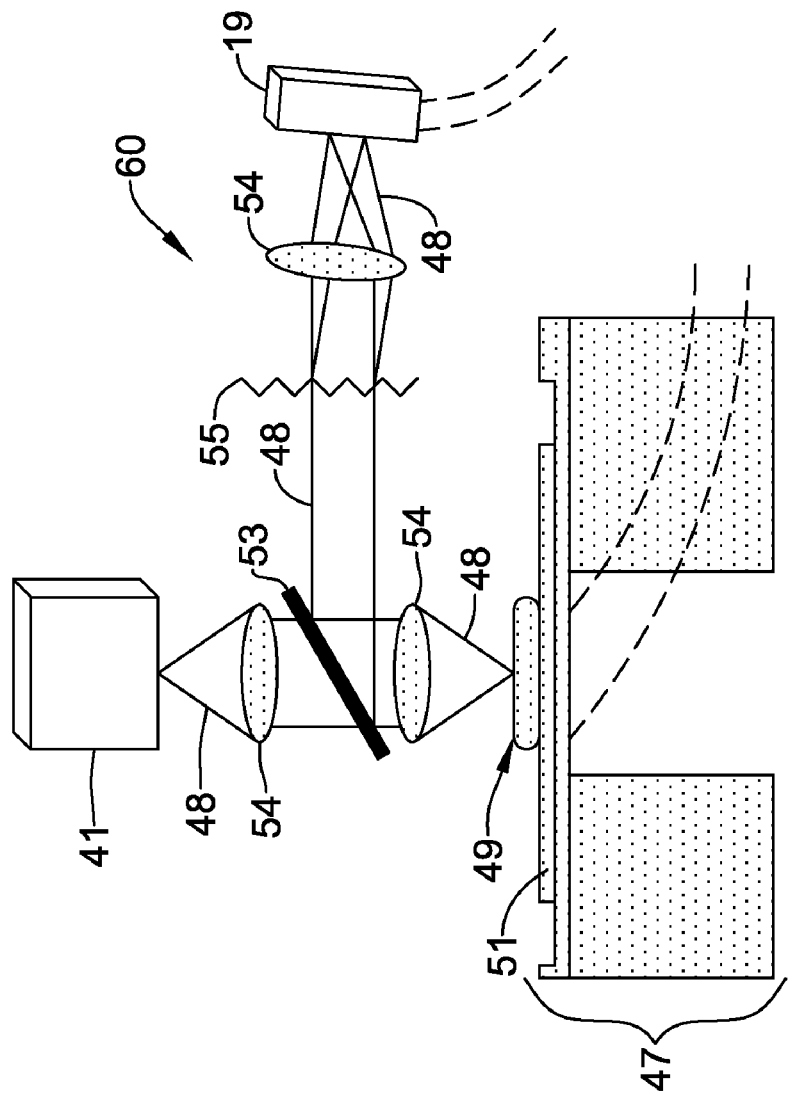

FIG. 12 shows an illustrative example of a surface-enhanced Raman spectrometer, configuration or device 60 relative to a PHASED detector structure 47. A VCSEL 41 may emit light 48 which may, via possible optics 54, impinge a surface-enhanced Raman spectrometer film 49 situated on a heater membrane 51. Heater membrane 49 may be part of a PHASED structure 47. Light 48 may be reflected by film 49 to a notch or edge filter 53 which may or may not have the properties of a splitter. Filter 53 appears to have the properties of a splitter for the illustrative example in FIG. 12. Filter 53 may reflect certain light 48 in accordance with the specifications of the filter to through a transmissive grating 55. In some configurations, this grating may be reflective. From grating 55, light 48 may continue on to a micro CCD array 19, via possible optics. Array 19 may have a TE cooler, if needed. PHASED structure 47 may have a TE cooler, if needed.

Figure 13:
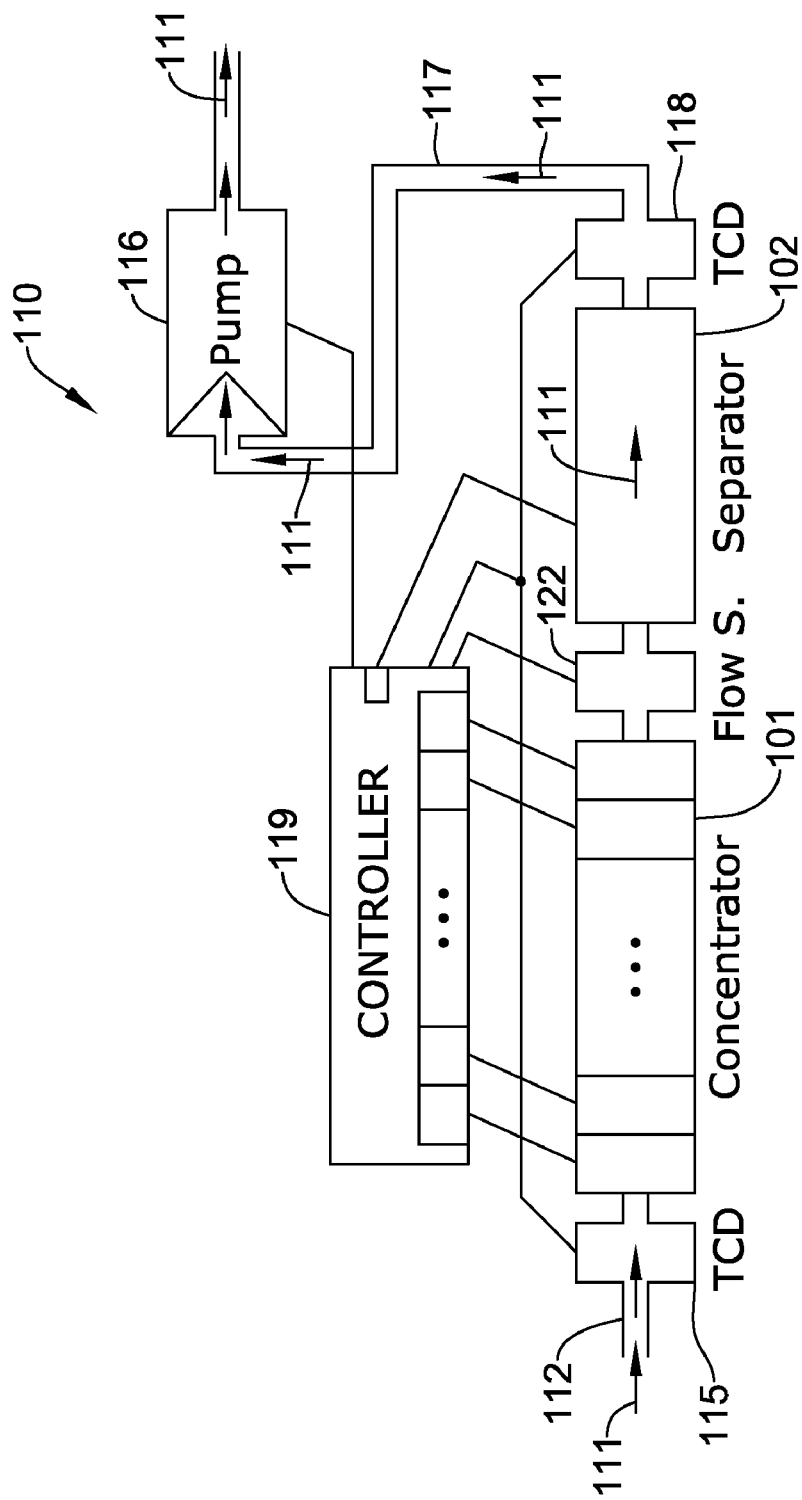
FIGS. 13-16 show an illustrative example of a fluid analyzer that may be used in conjunction with spectrometers.

A fluid analyzer which may be used in conjunction with the spectrometers 10, 20, 30, 40, 50 and 60 may include a channel or channels for a flow of a sample along a membrane that supports heaters and a stationary phase for sample analysis. The channel or channels may be an integral part of the micro fluid analyzer. The analyzer may have the pre-concentrator (PC) 101 (viz., concentrator) and chromatographic separator (CS) 102 that incorporates the channel or channels. FIG. 13 is a system view of an example fluid analyzer which may be a phased heater array structure for enhanced detection (PHASED) micro gas analyzer (MGA) 110. It reveals certain details of the micro gas apparatus 110 which may encompass the specially designed channel described herein. The PHASED MGA 110, and variants of it, may be used for various fluid chromatography applications.

Sample stream 111 may enter input port 112 to the first leg of a differential thermal-conductivity detector (TCD) (or other device) 115. A pump 116 may effect a flow of fluid 111 through the apparatus 110 via tube 117. There may be additional pumps, and various tube or plumbing arrangements or configurations for system 110 in FIG. 13. Fluid 111 may be moved through a TCD 115, concentrator 101, flow sensor 122, separator 102 and TCD 118. Controller 119 may manage the fluid flow, and the activities of concentrator 101 and separator 102. Controller 119 may be connected to TCD 115, concentrator 101, flow sensor 122, separator 102, TCD 118, and pump 116. Data from detectors 115 and 118, and sensor 122 may be sent to controller 119, which in turn may process the data. The term "fluid" may refer to a gas or a liquid, or both.

Figure 14:
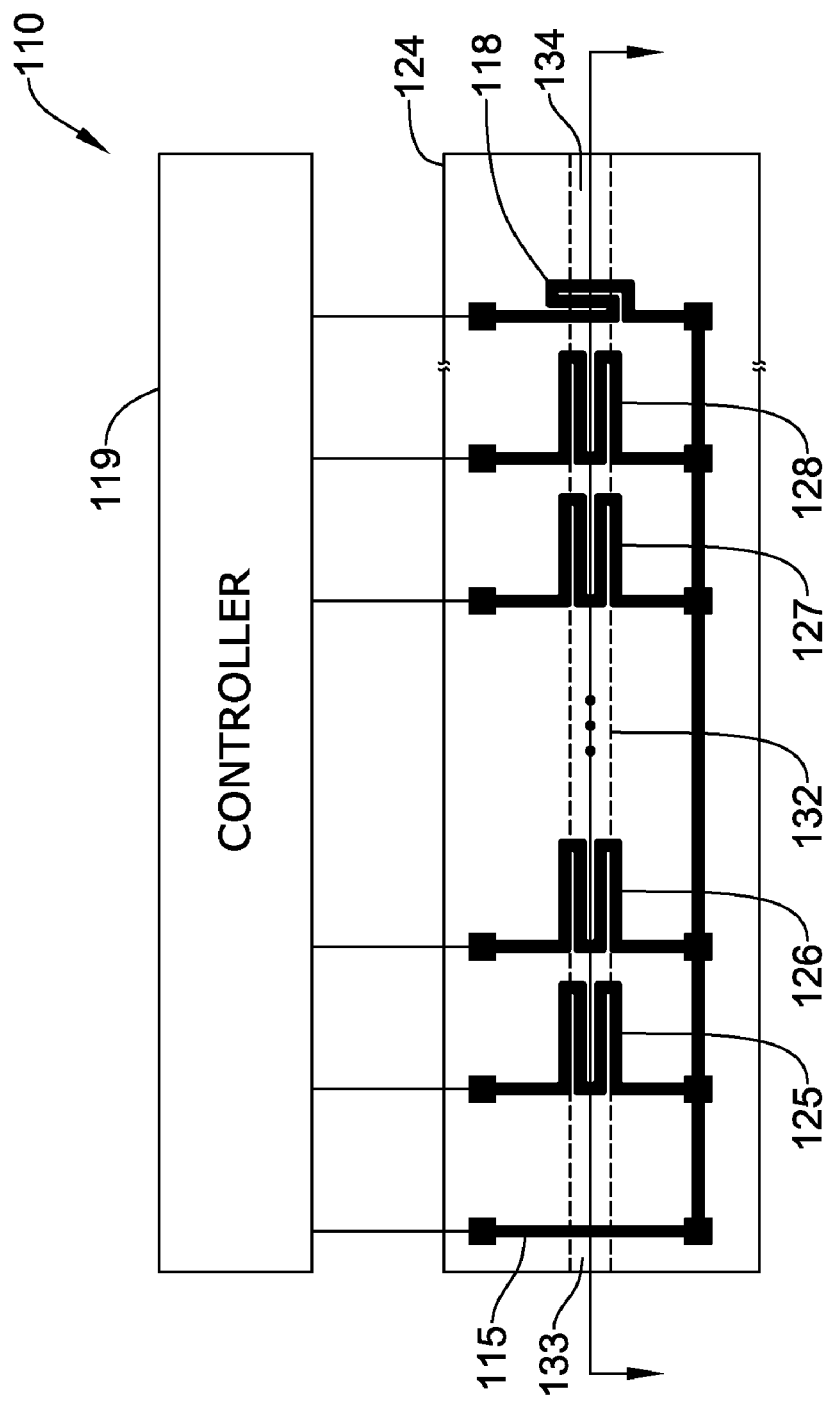

FIG. 14 is a schematic diagram of part of the sensor apparatus 110 representing a portion of concentrator 101 and/or separator 102 in FIG. 13. This part of sensor apparatus 110 may include a substrate or holder 124 and controller 119.

Controller 119 may or may not be incorporated into substrate 124. Substrate 124 may have a number of thin film heater elements 125, 126, 127, and 128 positioned thereon. While only four heater elements are shown, any number of heater elements may be provided, for instance, between two and one thousand, but typically in the 20-100 range. Heater elements 125, 126, 127, and 128 may be fabricated of any suitable electrical conductor, stable metal, alloy film, or other material. Heater elements 125, 126, 127, and 128 may be provided on a thin, low-thermal mass, low-in-plane thermal conduction, membrane or support member 124, as shown in FIGS. 14 and 15.

Figure 15:
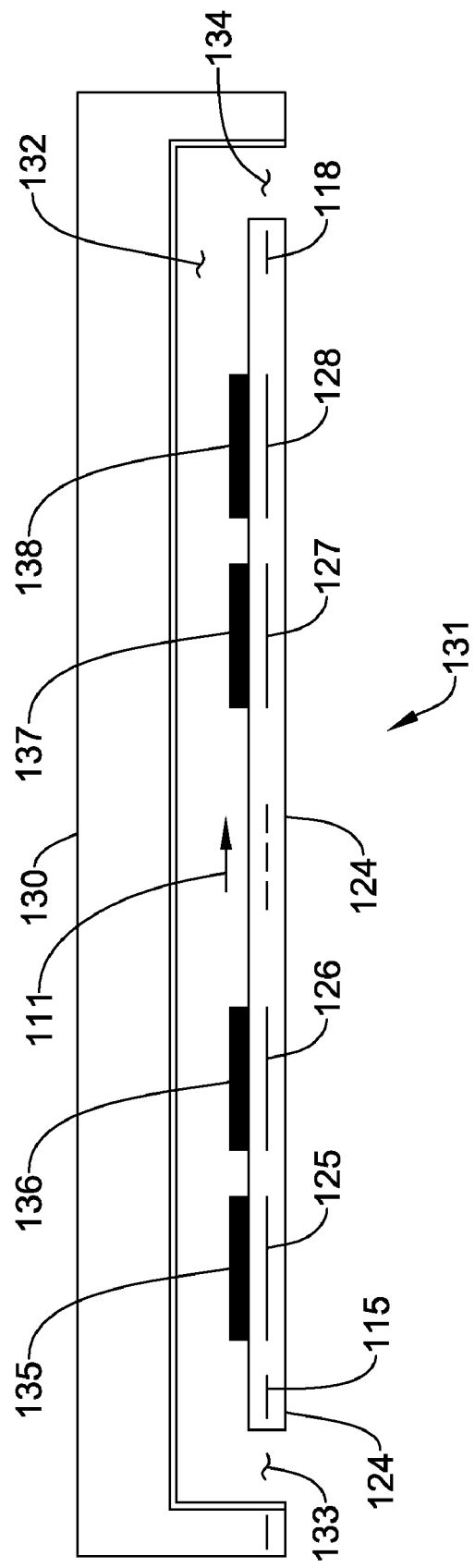

Substrate 130 may have a well-defined single-channel phased heater mechanism 131 having a channel 132 for receiving the sample fluid stream 111, as shown in FIG. 15. The channels may be fabricated by selectively etching silicon channel wafer substrate 130 near support member 124. The channel may include an entry port 133 and an exhaust port 134.

The sensor apparatus 110 may also include a number of interactive elements inside channel 132 so that they are exposed to the streaming sample fluid 111. Each of the interactive elements may be positioned adjacent, i.e., for closest possible contact, to a corresponding heater element. For example, in FIG. 15, interactive elements 135, 136, 137, and 138 may be provided on a surface of support member 124 in channel 132, and be adjacent to heater elements 125, 126, 127, and 128, respectively. There may be other channels with additional interactive film elements which are not shown in the present illustrative example. The interactive elements may be formed from any number of films commonly used in liquid or gas chromatography. Furthermore, the above interactive substances may be modified by suitable dopants to achieve varying degrees of polarity and/or hydrophobicity, to achieve optimal adsorption and/or separation of targeted analytes.

Controller 119 may be electrically connected to each of the heater elements 125, 126, 127, 128, and detectors 115 and 118 as shown in FIG. 14. Controller 119 may energize heater elements 125, 126, 127 and 128 in a time phased sequence (see bottom of FIG. 16) such that each of the corresponding interactive elements 135, 136, 137, and 138 become heated and desorb selected constituents into a streaming sample fluid 111 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 118, for detection and analysis.

Figure 16:
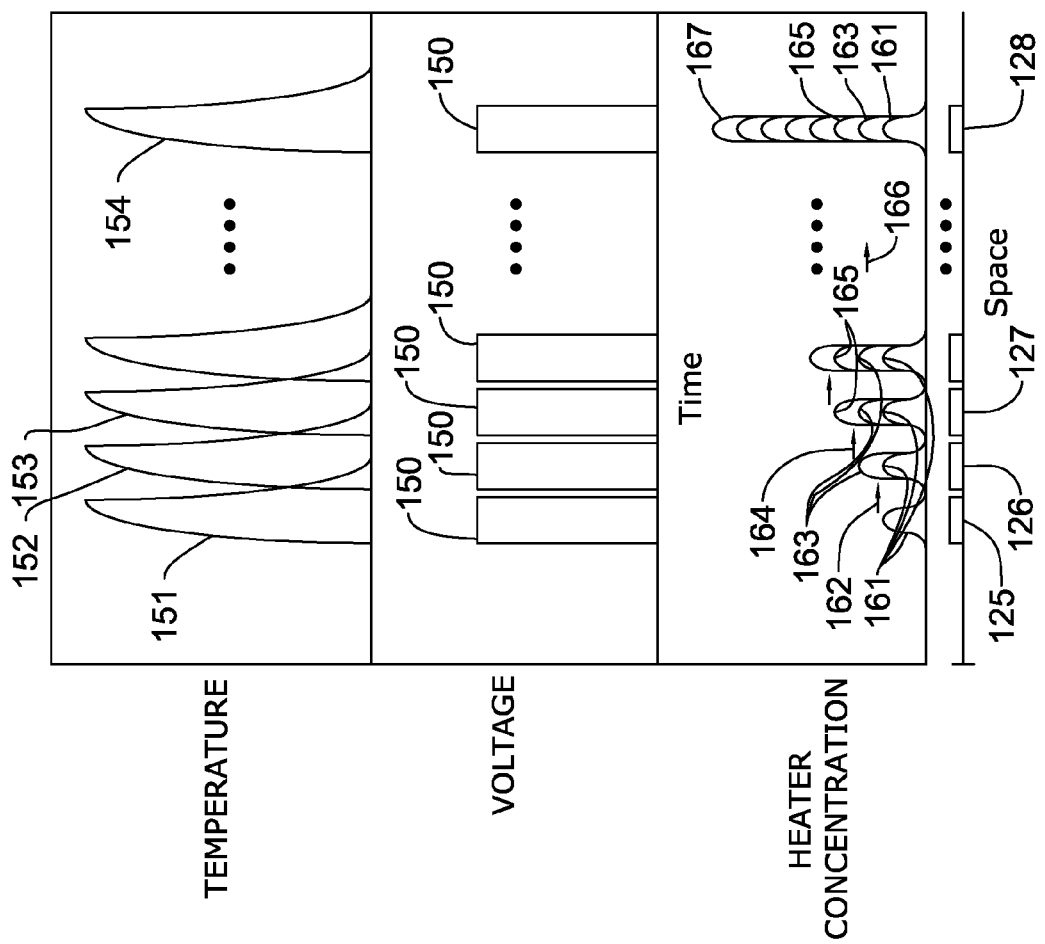

FIG. 16 is a graph showing illustrative relative heater temperatures, along with corresponding concentration pulses produced at each heater element. As indicated above, controller 119 may energize heater elements 125, 126, 127 and 128 in a time phased sequence with voltage signals 150. Time phased heater relative temperatures for heater elements 125, 126, 127, and 128 may be shown by temperature profiles or lines 151, 152, 153, and 154, respectively.

In the example shown, controller 119 (FIG. 14) may first energize first heater element 125 to increase its temperature as shown at line 151 of FIG. 16. Since first heater element 125 is thermally coupled to first interactive element 135 (FIG. 15), the first interactive element desorbs selected constituents into the streaming sample fluid 111 to produce a first concentration pulse 161 (FIG. 16) at the heater element 125, if no other heater elements were to be pulsed. The streaming sample fluid 111 carries the first concentration pulse 161 downstream toward second heater element 126, as shown by arrow 162.

Controller 119 may next energize second heater element 126 to increase its temperature as shown at line 152, starting at or before the energy pulse on element 125 has been stopped. Since second heater element 126 is thermally coupled to second interactive element 136, the second interactive element also desorbs selected constituents into streaming sample fluid 111 to produce a second concentration pulse. Controller 119 may energize second heater element 126 such that the second concentration pulse substantially overlaps first concentration pulse 161 to produce a higher concentration pulse 163, as shown in FIG. 16. The streaming sample fluid 111 may carry the larger concentration pulse 163 downstream toward third heater element 127, as shown by arrow 164.

Controller 119 may then energize third heater element 127 to increase its temperature as shown at line 153 in FIG. 16. Since third heater element 127 is thermally coupled to third interactive element 137, third interactive element 137 may desorb selected constituents into the streaming sample fluid to produce a third concentration pulse. Controller 119 may energize third heater element 127 such that the third concentration pulse substantially overlaps larger concentration pulse 163 provided by first and second heater elements 125 and 126 to produce an even larger concentration pulse 165. The streaming sample fluid 111 carries this larger concentration pulse 165 downstream toward an "Nth" heater element 128, as shown by arrow 166.

Controller 119 may then energize "N-th" heater element 128 to increase its temperature as shown at line 154. Since "N-th" heater element 128 is thermally coupled to an "N-th" interactive element 138, "N-th" interactive element 138 may desorb selected constituents into streaming sample fluid 111 to produce an "N-th" concentration pulse. Controller 119 may energize "N-th" heater element 128 such that the "N-th" concentration pulse substantially overlaps larger concentration pulse 165 provided by the previous N-1 interactive elements. The streaming sample fluid may carry the resultant "N-th" concentration pulse 167 to either a separator 102 or a detector 118.

Nomenclature used in here may include CCD (charge-coupled device), MDD (micro discharge device) and PD (photo detector). The symbols may include A (aperture or f-number, $N \cdot g/f = W/f$), d (distance (light source to grating) in μm), $D_i$ (dispersion of wavelengths of the image on the PD-CCD array, in nm (wavelength)/μm (length)), $D_g$ (dispersion of light generated by the grating, $D_g = (\lambda_2 - \lambda_1)/(s_2 - s_1) = (\lambda_2 - \lambda_1)/\{f \cdot (\sin \delta_2 - \sin \delta_1)\} = g/(f \cdot n))$, f (distance between grating and PD-CCD array, concave grating focal distance and diameter of the Rowland circle), g (grating groove center-center spacing in nm), N (number of grating grooves), $N_p$ (number of pixel elements in the PD-CCD array), p (pixel size in μm), s (space variable on the PD-CCD plane, $s_2 - s_1$ corresponding to $\lambda_2 - \lambda_1$), $s_w$ (thickness of the support of the MDD source, above the PD-CCD surface), W (width of the grating), δ (angle between rays incident to and output from the grating, i.e., diffraction angle as defined in FIG. 5 and in FIG. 2, $\delta = \arcsin\{(s_w/f)^{0.5}\}$), Δλ (wavelength range covered by each pixel, in nm), and λ (wavelength in nm, $\lambda_1$=smallest and $\lambda_2$=longest wavelength of a used range)

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An optical spectrometer comprising:
   a first wafer;
   a second wafer having a channel situated on the first wafer, the channel having a first portion and a second portion;
   a light source situated at a first end of the first portion of the channel;
   a reflector situated at a second end of the first portion of the channel and a first end of the second portion of the channel; and
   a detector array situated at a second end of the second portion of the channel; and
   wherein the light source, reflector and detector array are situated about a circumference of a circle in a plane; and
   the light source is a micro discharge device.

2. The spectrometer of claim 1, wherein the reflector is a concave diffraction grating, a holographic concave reflective grating, or a focusing transmission grating.

3. The spectrometer of claim 1, wherein the circle is a Rowland circle.

4. The spectrometer of claim 1, wherein:
   the first portion of the channel and the second portion of the channel are connected to each other; and
   a fluid flow channel has an inlet situated proximate to the light source, a path through the first portion of the channel and the second portion of the channel, and an outlet situated proximate to the detector array.

5. The spectrometer of claim 1, wherein the detector array is a photo-detector array.

6. The spectrometer of claim 1, wherein the first and second wafers and the first and second channels may be fabricated with MEMS (micromachined electro mechanical system) technology.

7. The spectrometer of claim 2, wherein the grating comprises a set of grating grooves or a holographic grating having dimensions compatible with a spectrum or spectrums to be observed within the spectrometer.

8. A spectrometer comprising:
   a first wafer;
   a detector situated on the first wafer;
   a second wafer situated on the first wafer, having a first opening about the detector, and having a light source;
   a third wafer, situated on the second wafer, having a second opening approximately aligned with the first opening, and having a channel intersecting the first and second openings; and
   a fourth wafer situated on the third wafer, and having a reflector-grating situated proximate to the second opening; and
   wherein the light source is a micro discharge device.

9. The spectrometer of claim 8, wherein a light path is available from the light source to the reflector-grating, and from the reflector-grating to the detector.

10. The spectrometer of claim 8, wherein:
    the detector is a photo-detector.

11. The spectrometer of claim 8, wherein the light source, the reflector-grating and the detector are situated proximate to a circumference of a circle.

12. The spectrometer of claim 8, wherein the light source is an end of an optical fiber having another end coupled to a source of light.

13. A spectrometer comprising:
    a first wafer;
    a detector situated on the first wafer;
    a second wafer situated on the first wafer, having a first opening about the detector, and having a light source;
    a third wafer, situated on the second wafer, having a second opening approximately aligned with the first opening, and having a channel intersecting the first and second openings; and
    a fourth wafer situated on the third wafer, and having a reflector-grating situated proximate to the second opening; and
    wherein the light source is a micro discharge device; and
    the detector is a photo-detector.

* * * * *